United States Patent
Kondreddi et al.

(10) Patent No.: US 9,546,138 B2
(45) Date of Patent: Jan. 17, 2017

(54) PYRIDONE DERIVATIVES AND USES THEREOF IN THE TREATMENT OF TUBERCULOSIS

(71) Applicants: Ravinder Reddy Kondreddi, Singapore (SG); Ngai Ling Ma, Vic (AU); Stefan Peukert, Arlington, MA (US); Srinivasa P S Rao, Singapore (SG); Manjunatha Ujjini, Singapore (SG)

(72) Inventors: Ravinder Reddy Kondreddi, Singapore (SG); Ngai Ling Ma, Vic (AU); Stefan Peukert, Arlington, MA (US); Srinivasa P S Rao, Singapore (SG); Manjunatha Ujjini, Singapore (SG)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/648,217

(22) PCT Filed: Dec. 12, 2013

(86) PCT No.: PCT/US2013/074632
§ 371 (c)(1),
(2) Date: May 28, 2015

(87) PCT Pub. No.: WO2014/093606
PCT Pub. Date: Jun. 19, 2014

(65) Prior Publication Data
US 2015/0291526 A1 Oct. 15, 2015

Related U.S. Application Data

(60) Provisional application No. 61/736,921, filed on Dec. 13, 2012.

(51) Int. Cl.
| | | |
|---|---|---|
| *C07D 213/69* | (2006.01) | |
| *C07F 9/58* | (2006.01) | |
| *C07D 401/06* | (2006.01) | |
| *C07D 405/06* | (2006.01) | |
| *C07D 213/64* | (2006.01) | |
| *A61K 31/4412* | (2006.01) | |
| *A61K 31/4433* | (2006.01) | |
| *A61K 31/4439* | (2006.01) | |
| *A61K 31/444* | (2006.01) | |
| *A61K 31/675* | (2006.01) | |
| *A61K 45/06* | (2006.01) | |
| *C07D 401/04* | (2006.01) | |

(52) U.S. Cl.
CPC ........... *C07D 213/69* (2013.01); *A61K 31/444* (2013.01); *A61K 31/4412* (2013.01); *A61K 31/4433* (2013.01); *A61K 31/4439* (2013.01); *A61K 31/675* (2013.01); *A61K 45/06* (2013.01); *C07D 213/64* (2013.01); *C07D 401/04* (2013.01); *C07D 401/06* (2013.01); *C07D 405/06* (2013.01); *C07F 9/581* (2013.01)

(58) Field of Classification Search
CPC .................................. C07D 213/69; C07F 9/58
USPC ........................ 546/24, 25, 296; 514/89, 348
See application file for complete search history.

(56) References Cited

U.S. PATENT DOCUMENTS

2010/0069440 A1    3/2010    Moore et al.

FOREIGN PATENT DOCUMENTS

| WO | 0102008 A1 | 1/2001 |
|---|---|---|
| WO | 03068230 A1 | 8/2003 |
| WO | 03103668 A1 | 12/2003 |
| WO | 2007089634 A2 | 8/2007 |
| WO | 2009143180 A1 | 11/2009 |
| WO | 2012049161 A1 | 4/2012 |

OTHER PUBLICATIONS

Kremer et al., "Current Status and Future Development of Antitubercular Chemotherapy" Expert Opinion Investig. Drugs, 11(8)1033-1049, 2002.
Frieden et al., "Tuberculosis" The Lancet 362:887-99, 2003.
Diacon et al., "The Diarylquinoline TMC207 for Multidrug-Resistant Tuberculosis" New England Journal of Medicine 360(23):2397-2405, Jun. 4, 2009.
Davies and Yew, "Recent Developments in the Treatment of Tuberculosis" Expert Opinion Investig Drugs 12:1297-1312, 2003.
Uhlin et al., "Adjunct Immunotherapies for Tuberculosis" Journal Infectious Diseases 205(Suppl 2),S325-334, 2012.
Kafka and Kappe, "Synthesis of 4-Hydrozxy-2(1H)-Pyridones from Azomethines and Substituted Dialkylmalonates" Monatshefte fuer Chemie 128(10):1019-1031, 1997.

(Continued)

*Primary Examiner* — Patricia L Morris
(74) *Attorney, Agent, or Firm* — Chihang Amy Smith; Genomics Institute of the Novartis Research Foundation

(57) ABSTRACT

A compound of Formula (I) is provided that has been shown to be useful for treating a disease, disorder or syndrome that is mediated by the inhibition of mycolic acid biosynthesis through inhibition of *M. tuberculosis* Enoyl Acyl Carrier Protein Reductase enzyme (InhA):

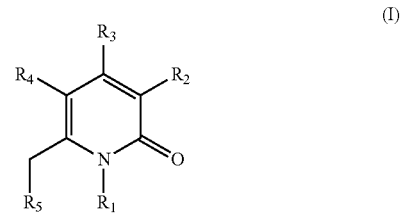

(I)

wherein $R_1$, $R_2$, $R_3$, $R_4$ and $R^5$ are as defined herein.

17 Claims, No Drawings

(56) References Cited

OTHER PUBLICATIONS

Rowley et al., "5,6,7,8-Tetrahydroquinolones as Antagonists at the Glycine Site of the NMDA Receptor" Bioorganic and Medicinal Chemistry Letters 5(18):2089-92, 1995.
Dannhardt et al., "Anti-Mycobacterial 7-Hydroxy-2,3-dihydro-1H-Indolizin-5-Ones" European Journal of Medicinal Chemistry 22(6), 505-10, 1987.
Dannhardt et al., "Anti-Mycobacterial 4-Hydroxy-3-Phenylpyridin-2 (1H)-ones" European Journal of Medicinal Chemistry 26:599-604, 1991.

PYRIDONE DERIVATIVES AND USES THEREOF IN THE TREATMENT OF TUBERCULOSIS

CROSS-REFERENCE TO RELATED APPLICATIONS

This application is a U.S. National Phase filing of International Application Serial No. PCT/US2013/074632, filed 12 Dec. 2013, and claims priority to U.S. Patent Application No. 61/736,921, filed 13 Dec. 2012, the contents of which are incorporated herein by reference in their entirety.

This application claims priority to U.S. Patent Application No. 61/736,921, filed 13 Dec. 2012, the contents of which are incorporated herein by reference in their entirety.

FIELD OF THE INVENTION

The present invention relates to pyridone derivatives, pharmaceutical formulations thereof, and their use for the treatment of tuberculosis, in particular multi-drug resistant (MDR) and extensively drug-resistant (XDR) tuberculosis.

BACKGROUND

Until tuberculosis is controlled worldwide, it will continue to be a major killer in less developed countries and a constant threat in most of the more-developed countries. It has been reported that 2 billion people are latently infected and 1 in 10 latent infections will progress to the active disease. *Mycobacterium tuberculosis*, the causative agent for tuberculosis (TB), infects one-third of the world's population, resulting in eight to nine million new cases of active TB and two million deaths each year (Kremer, et al., *Expert Opin. Investig. Drugs*, 11, 1033-1049 (2002); and Frieden, T. R., et al., *The Lancet*, 362, 887-99 (2003); and Diacon, Andreas H., et al., *N Eng J Med*, 360(23), 2397-2405 (2009)). TB is presently treated with a four-drug combination (isoniazid, rifampin, pyrazinamide, ethambutol) that imposes a lengthy 6-9 month treatment course, often under the direct observation of a healthcare provider (Davies, et al., *Expert Opin. Investig. Drugs*, 12, 1297-1312 (2003)). The major shortcoming of this regimen is the long treatment time (up to 2 years) and high failure rate, which makes patient compliance and proper implementation a challenge. More than two-thirds of the TB patients do not receive full and proper TB treatment, which results in a high relapse rate and emergence of drug resistance.

About 4% of the TB cases worldwide are multiple-drug resistant (MDR), e.g., resistant to both isoniazid and rifampicin. XDR-TB, an abbreviation for extensively drug-resistant tuberculosis (TB), is a form of TB which is resistant to at least four of the core anti-TB drugs. XDR-TB involves resistance to the two most powerful anti-TB drugs, isoniazid and rifampicin (MDR-TB), in addition to resistance to any of the fluoroquinolones (such as ofloxacin or moxifloxacin) and to at least one of three injectable second-line drugs (amikacin, capreomycin or kanamycin). Although XDR-TB is rarer, 77 countries worldwide had reported at least one case by the end of 2011. The World Health Organization (WHO) estimates that there are about 650,000 MDR-TB cases in the world at any one time. The number of cases of MDR tuberculosis is alarmingly increasing worldwide, with MDR detected in up to 35% of newly diagnosed cases and in 76.5% of patients who had previously been treated for tuberculosis. XDR tuberculosis was identified in 14% of patients with MDR, with patients less than 35 years old exhibiting odds of MDR tuberculosis that was 2 times that for individuals aged over 35 years. See, Uhlin, M., et al., *J Infect Dis*, 205 (Suppl 2), S325-334 (2012).

MDR-TB and XDR-TB both take substantially longer to treat than ordinary (drug-susceptible) TB, and require the use of second-line anti-TB drugs, which are more expensive and have more side-effects than the first-line drugs used for drug-susceptible TB. Treatment is complex and requires longer use of more-expensive, less effective and toxic anti-tuberculosis drugs, which results in high morbidity and mortality.

There still remain several issues that need to be addressed in both standard TB therapies as well as MDR/XDR resistant therapies. For example, there is a need to shorten the duration of standard TB therapy which could increase compliance and thus reduce resistance. For MDR/XDR resistant TB, there is an unmet need to find novel chemotypes that are active against MDR and XDR TB that enhance cure rate, reduce adverse effects, shorten treatment time, and improve patient compliance which reduces resistance.

SUMMARY

The compounds described herein have been shown to be useful in the treatment of tuberculosis, in particular multi-drug resistant (MDR) and extensively drug-resistant (XDR) tuberculosis.

One aspect of the present invention provides compounds of Formula (I)

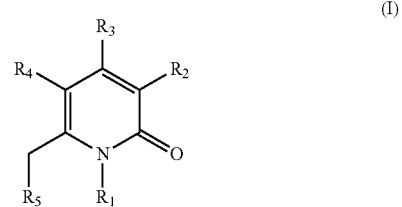

wherein
$R_1$ is H, methyl or ethyl;
$R_2$ is phenyl, pyrrole or pyrazole, wherein said phenyl is optionally substituted with one or more substituents independently selected from fluoro or chloro; provided that when said substituent is chloro, said chloro is on the meta or ortho position of said phenyl and the number of chloro substituent is not more than one;
$R_3$ is a structural formula selected from the group consisting of

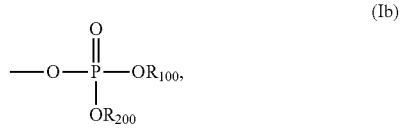

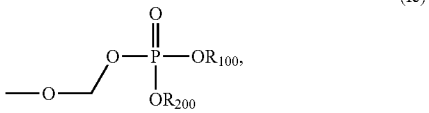

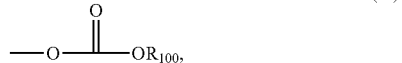

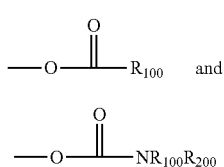

where $R_{100}$ and $R_{200}$ are each independently selected from the group consisting of H, $(C_1-C_6)$alkyl, cycloalkyl, an organic cation and an inorganic cation;

$R_4$ is H or —C(=O)NH$_2$;

$R_5$ is selected from the group consisting of $(C_1-C_6)$alkyl, cycloalkyl, phenyl, heterocycle and heteroaryl, optionally substituted with one or more independent $R_{300}$ substituents; and $R_{300}$ is selected from the group consisting of H, $(C_1-C_6)$ alkyl, cycloalkyl, hydroxy, amino and F;

or a pharmaceutically acceptable salt thereof.

In one embodiment, the compound of Formula (I) is provided wherein $R_1$ is H; or a pharmaceutically acceptable salt thereof. In another embodiment, a compound of Formula (I) is provided wherein $R_2$ is phenyl; or a pharmaceutically acceptable salt thereof. In still another embodiment, a compound of Formula (I) is provided wherein $R_3$ is (Ia); or a pharmaceutically acceptable salt thereof.

In one embodiment, the compound of Formula (I) is provided wherein $R_3$ is (Ic), and $R_{100}$ and $R_{200}$ are both H; or a pharmaceutically acceptable salt thereof. In another embodiment, a compound of Formula (I) is provided wherein $R_4$ is H; or a pharmaceutically acceptable salt thereof. In still another embodiment, a compound of Formula (I) is provided wherein $R_5$ is $(C_1-C_6)$alkyl, phenyl, tetrahydro-2H-pyran or pyridine; or a pharmaceutically acceptable salt thereof.

In one embodiment, the compound of Formula (I) is provided wherein $R_5$ is cycloalkyl; or a pharmaceutically acceptable salt thereof. In another embodiment, a compound of Formula (I) is provided wherein $R_5$ is cyclohexane; or a pharmaceutically acceptable salt thereof. In still another embodiment, a compound of Formula (I) is provided wherein $R_5$ is cyclohexane which is substituted with one or more substituents independently selected from $(C_1-C_6)$alkyl, cycloalkyl or F; or a pharmaceutically acceptable salt thereof. In still another embodiment, a compound of Formula (I) is provided wherein $R_5$ is cyclohexane which is substituted with one or more substituents independently selected from methyl, cyclopropane or F; or a pharmaceutically acceptable salt thereof. In still another embodiment, a compound of Formula (I) is provided wherein $R_5$ is cyclohexane which is substituted with two methyl substituents; or a pharmaceutically acceptable salt thereof.

Representative compounds of Formula (I), or a pharmaceutically acceptable salt thereof, are present in the following Table 1:

TABLE 1

| Compound No. | Compound Structure | Compound Chemical Name |
|---|---|---|
| PD1 | 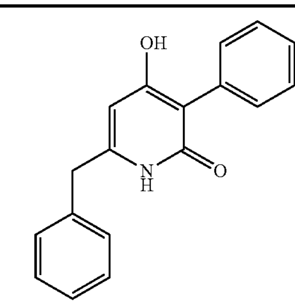 | 6-benzyl-4-hydroxy-3-phenylpyridin-2(1H)-one, |
| PD2 | 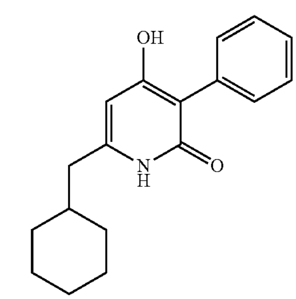 [SMILES: O=c1[nH]c(CC2CCCCC2)cc(O)c1-c1ccccc1] | 6-(cyclohexylmethyl)-4-hydroxy-3-phenylpyridin-2(1H)-one, |
| PD3 | 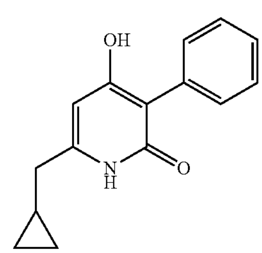 [SMILES: O=c1[nH]c(CC2CC2)cc(O)c1-c1ccccc1] | 6-(cyclopropylmethyl)-4-hydroxy-3-phenylpyridin-2(1H)-one, |

TABLE 1-continued
| Compound No. | Compound Structure | Compound Chemical Name |
| --- | --- | --- |
| PD4 | 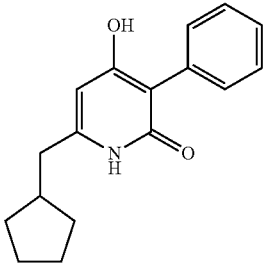 [SMILES: O=c1[nH]c(CC2CCCC2)cc(O)c1-c1ccccc1] | 6-(cyclopentylmethyl)-4-hydroxy-3-phenylpyridin-2(1H)-one, |
| PD5 | 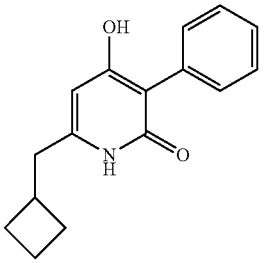 [SMILES: O=c1[nH]c(CC2CCC2)cc(O)c1-c1ccccc1] | 6-(cyclobutylmethyl)-4-hydroxy-3-phenylpyridin-2(1H)-one, |
| PD6 | 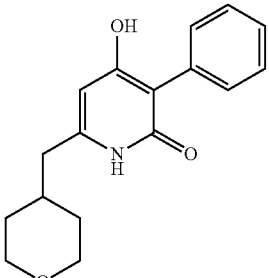 | 4-hydroxy-3-phenyl-6-((tetrahydro-2H-pyran-4-yl)methyl)pyridin-2(1H)-one, |
| PD7 | 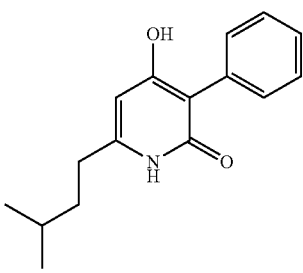 [SMILES: CC(C)CCc1cc(O)c(-c2ccccc2)c(=O)[nH]1] | 4-hydroxy-6-isopentyl-3-phenylpyridin-2(1H)-one, |
| PD8 | 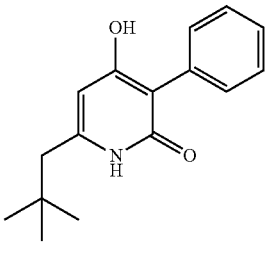 | 4-hydroxy-6-neopentyl-3-phenylpyridin-2(1H)-one, |

TABLE 1-continued
| Compound No. | Compound Structure | Compound Chemical Name |
|---|---|---|
| PD9 | 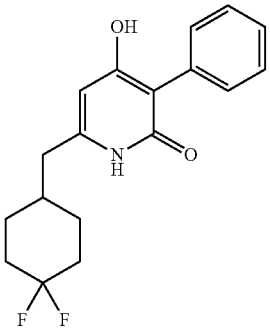 [SMILES: O=c1[nH]c(CC2CCC(F)(F)CC2)cc(O)c1-c1ccccc1] | 6-((4,4-difluorocyclohexyl)methyl)-4-hydroxy-3-phenylpyridin-2(1H)-one, |
| PD10 | 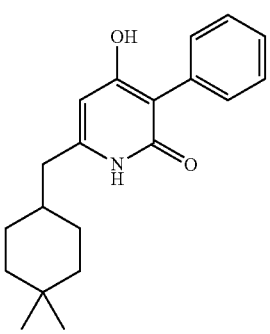 [SMILES: CC1(C)CCC(Cc2cc(O)c(-c3ccccc3)c(=O)[nH]2)CC1] | 6-((4,4-dimethylcyclohexyl)methyl)-4-hydroxy-3-phenylpyridin-2(1H)-one, |
| PD11 | 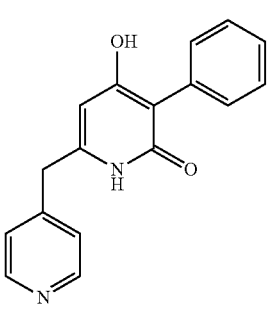 [SMILES: O=c1[nH]c(Cc2ccncc2)cc(O)c1-c1ccccc1] | 4-hydroxy-3-phenyl-6-(pyridin-4-ylmethyl)pyridin-2(1H)-one, |
| PD12 | 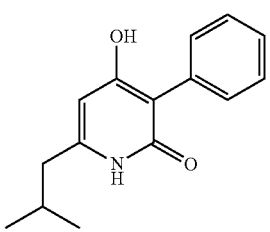 [SMILES: CC(C)Cc1cc(O)c(-c2ccccc2)c(=O)[nH]1] | 4-hydroxy-6-isobutyl-3-phenylpyridin-2(1H)-one, |
| PD13 | 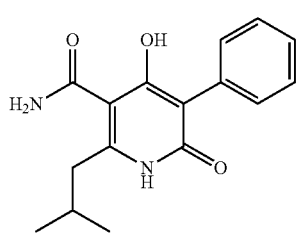 [SMILES: CC(C)Cc1[nH]c(=O)c(-c2ccccc2)c(O)c1C(N)=O] | 4-hydroxy-2-isobutyl-6-oxo-5-phenyl-1,6-dihydropyridine-3-carboxamide, |

TABLE 1-continued

| Compound No. | Compound Structure | Compound Chemical Name |
|---|---|---|
| PD14 | 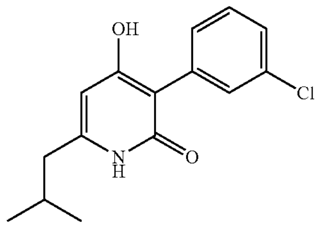 [SMILES: CC(C)Cc1cc(O)c(-c2cccc(Cl)c2)c(=O)[nH]1] | 3-(3-chlorophenyl)-4-hydroxy-6-isobutylpyridin-2(1H)-one, |
| PD15 | 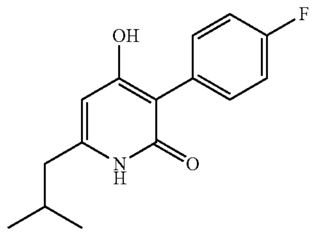 [SMILES: CC(C)Cc1cc(O)c(-c2ccc(F)cc2)c(=O)[nH]1] | 3-(4-fluorophenyl)-4-hydroxy-6-isobutylpyridin-2(1H)-one, |
| PD16 | 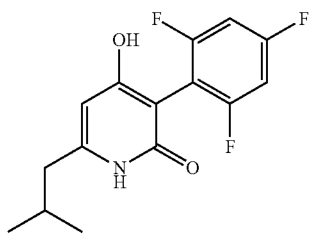 [SMILES: CC(C)Cc1cc(O)c(-c2c(F)cc(F)cc2F)c(=O)[nH]1] | 4-hydroxy-6-isobutyl-3-(2,4,6-trifluorophenyl)pyridin-2(1H)-one, |
| PD17 | 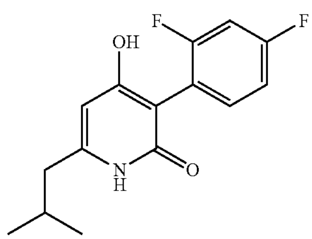 [SMILES: CC(C)Cc1cc(O)c(-c2ccc(F)cc2F)c(=O)[nH]1] | 3-(2,4-difluorophenyl)-4-hydroxy-6-isobutylpyridin-2(1H)-one, |
| PD18 | 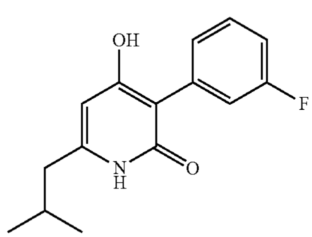 [SMILES: CC(C)Cc1cc(O)c(-c2cccc(F)c2)c(=O)[nH]1] | 3-(3-fluorophenyl)-4-hydroxy-6-isobutylpyridin-2(1H)-one, |
| PD19 | 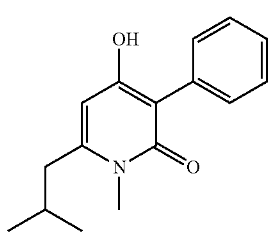 [SMILES: CC(C)Cc1cc(O)c(-c2ccccc2)c(=O)n1C] | 4-hydroxy-6-isobutyl-1-methyl-3-phenylpyridin-2(1H)-one, |

TABLE 1-continued

| Compound No. | Compound Structure | Compound Chemical Name |
|---|---|---|
| PD20 | 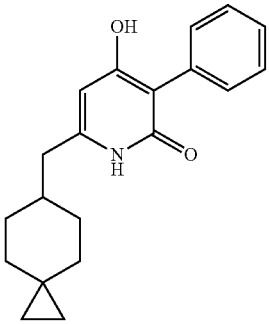 [SMILES: O=c1[nH]c(CC2CCC3(CC2)CC3)cc(O)c1-c1ccccc1] | 4-hydroxy-3-phenyl-6-(spiro[2.5]octan-6-ylmethyl)pyridin-2(1H)-one, |
| PD21 | 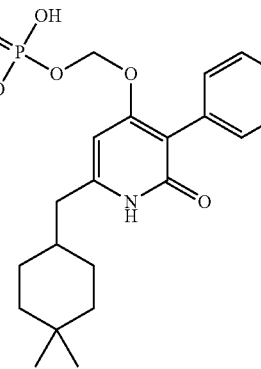 | ((6-((4,4-dimethylcyclohexyl)methyl)-2-oxo-3-phenyl-1,2-dihydropyridin-4-yl)oxy)methyl dihydrogen phosphate, |
| PD22 | 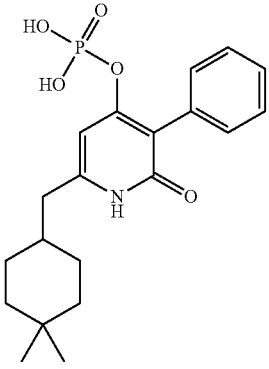 [SMILES: CC1(C)CCC(Cc2cc(OP(=O)(O)O)c(-c3ccccc3)c(=O)[nH]2)CC1] | 6-((4,4-dimethylcyclohexyl)methyl)-2-oxo-3-phenyl-1,2-dihydropyridin-4-dihydrogen phosphate, |
| PD23 | 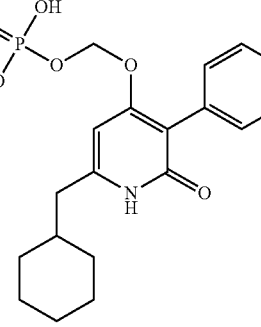 | ((6-(cyclohexylmethyl)-2-oxo-3-phenyl-1,2-dihydropyridin-4-yl)oxy)methyl dihydrogen phosphate, |

TABLE 1-continued
| Compound No. | Compound Structure | Compound Chemical Name |
|---|---|---|
| PD24 | 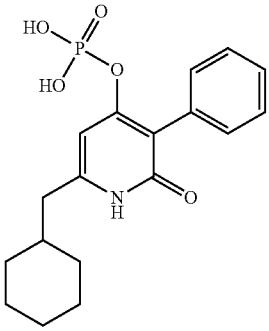 [SMILES: O=c1[nH]c(CC2CCCCC2)cc(OP(=O)(O)O)c1-c1ccccc1] | 6-(cyclohexylmethyl)-2-oxo-3-phenyl-1,2-dihydropyridin-4-yl dihydrogen phosphate, |
| PD25 | 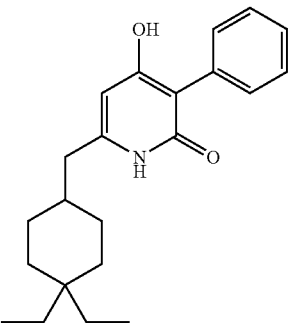 [SMILES: CCC1(CC)CCC(Cc2cc(O)c(-c3ccccc3)c(=O)[nH]2)CC1] | 6-((4,4-diethylcyclohexyl)methyl)-4-hydroxy-3-phenylpyridin-2(1H)-one, |
| PD26 | 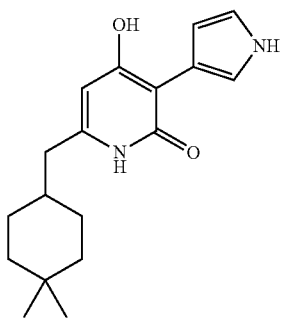 [SMILES: CC1(C)CCC(Cc2cc(O)c(-c3cc[nH]c3)c(=O)[nH]2)CC1] | 6-((4,4-dimethylcyclohexyl)methyl)-4-hydroxy-3-(1H-pyrrol-3-yl)pyridin-2(1H)-one, |
| PD27 | 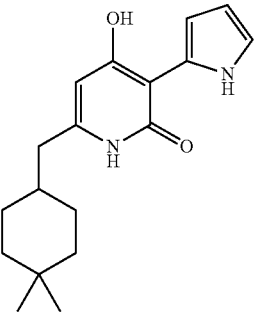 [SMILES: CC1(C)CCC(Cc2cc(O)c(-c3ccc[nH]3)c(=O)[nH]2)CC1] | 6-((4,4-dimethylcyclohexyl)methyl)-4-hydroxy-3-(1H-pyrrol-2-yl)pyridin-2(1H)-one, |

TABLE 1-continued

| Compound No. | Compound Structure | Compound Chemical Name |
|---|---|---|
| PD28 | 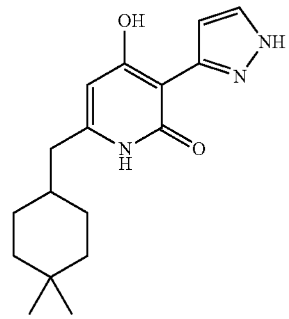 [SMILES: CC1(C)CCC(Cc2cc(O)c(-c3cc[nH]n3)c(=O)[nH]2)CC1] | 6-((4,4-dimethylcyclohexyl)methyl)-4-hydroxy-3-(1H-pyrazol-3-yl)pyridin-2(1H)-one, and |
| PD29 | 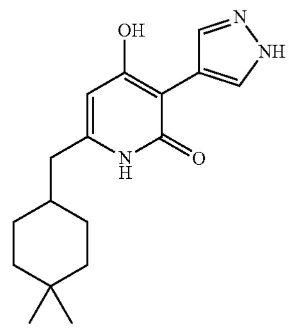 [SMILES: CC1(C)CCC(Cc2cc(O)c(-c3cn[nH]c3)c(=O)[nH]2)CC1] | 6-((4,4-dimethylcyclohexyl)methyl)-4-hydroxy-3-(1H-pyrazol-4-yl)pyridin-2(1H)-one. |

Compounds of particular interest, or a pharmaceutically acceptable salt thereof, are present in the following Table 2:

TABLE 2

| Compound No. | Compound Structure | Compound Chemical Name |
|---|---|---|
| PD10 | 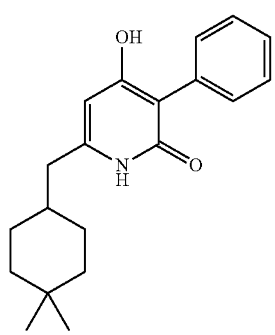 [SMILES: CC1(C)CCC(Cc2cc(O)c(-c3ccccc3)c(=O)[nH]2)CC1] | 6-((4,4-dimethylcyclohexyl)methyl)-4-hydroxy-3-phenylpyridin-2(1H)-one, |
| PD21 | 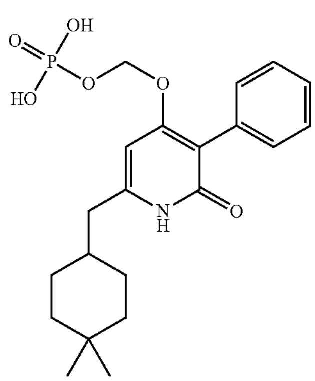 [SMILES: CC1(C)CCC(Cc2cc(OCOP(=O)(O)O)c(-c3ccccc3)c(=O)[nH]2)CC1] | ((6-((4,4-dimethylcyclohexyl)methyl)-2-oxo-3-phenyl-1,2-dihydropyridin-4-yl)oxy)methyl dihydrogen phosphate, and |

TABLE 2-continued

| Compound No. | Compound Structure | Compound Chemical Name |
| --- | --- | --- |
| PD22 | 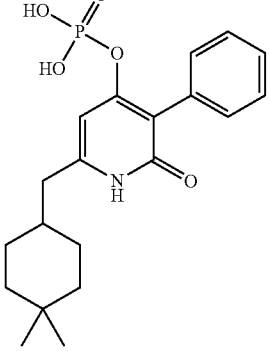 | 6-((4,4-dimethylcyclohexyl)methyl)-2-oxo-3-phenyl-1,2-dihydropyridin-4-dihydrogen phosphate. |

Another aspect of the present invention includes a pharmaceutical composition comprising a compound of Formula (I) compromising any one of embodiments described above, or a pharmaceutically acceptable salt thereof, and a pharmaceutically acceptable carrier or excipient. The pharmaceutical composition may further comprise at least one additional pharmaceutical agent described herein below. Additional pharmaceutical agents of particular interest are antituberculosis agents. Examples of antituberculosis agent include isoniazid, rifampicin, pyrazinamide, ethambutol, streptomycin, kanamycin, amikacin, capreomycin, ofloxacin, levofloxacin, moxifloxacin, cycloserine, para-aminosalicylic acid, ethioamide, prothionamide, thioacetazone clofazimine, amoxicilin with clavulanate, imipenem, linezolid, clarithromycin, and thioridazine.

In yet another aspect of the present invention, a method is provided for treating a disease, disorder or syndrome mediated by the inhibition of mycolic acid biosynthesis through inhibition of *M. tuberculosis* Enoyl Acyl Carrier Protein Reductase enzyme (InhA) comprising the step of administering to a patient (in particular, a human) in need thereof, a compound of Formula (I) including any of the embodiments described herein, or a pharmaceutically acceptable salt thereof. The disease, disorder or syndrome of particular interest is tuberculosis. In a particular useful embodiment, the human has (i) a sputum smear-positive, sputum smear-negative, or extrapulmonary tuberculosis; (ii) tuberculosis caused by drug resistant *Mycobacterium tuberculosis* complex (*M. tuberculosis*) organisms; or (iii) tuberculosis combined with human immunodeficiency virus (HIV) infection. The compound may be administered as a pharmaceutical composition described herein Another aspect of the present invention includes a compound according to Formula (I), for use in therapy (e.g., the use of a compound of Formula (I) for the treatment of a disease, disorder, or syndrome mediated by the inhibition of mycolic acid biosynthesis through inhibition of *M. tuberculosis* Enoyl Acyl Carrier Protein Reductase enzyme (InhA).

In yet another aspect of the present invention, a method is provided for treating a disease, disorder or syndrome mediated by the inhibition of mycolic acid biosynthesis through inhibition of *M. tuberculosis* Enoyl Acyl Carrier Protein Reductase enzyme (InhA) comprising the step of administering to a patient (in particular, a human) in need thereof
(i) a first composition comprising any one of the compounds according to claims 1 through 16, or a pharmaceutically acceptable salt thereof, and a pharmaceutically acceptable carrier or excipient; and
(ii) a second composition comprising at least one additional pharmaceutical agent and a pharmaceutically acceptable carrier or excipient. The disease, disorder or syndrome of particular interest is tuberculosis. In one embodiment, the human has (i) a sputum smear-positive, sputum smear-negative, or extrapulmonary tuberculosis; (ii) tuberculosis caused by drug resistant *Mycobacterium tuberculosis* complex (*M. tuberculosis*) organisms; or (iii) tuberculosis combined with human immunodeficiency virus (HIV) infection. The first and second compositions may be administered simultaneously; or sequentially in any order.

DEFINITIONS

As used herein, the terms "alkyl" refers to a hydrocarbon radical of the general formula $C_nH_{2n+1}$. The alkane radical may be straight or branched. For example, the term "($C_1$-$C_6$)alkyl" refers to a monovalent, straight, or branched aliphatic group containing 1 to 6 carbon atoms (e.g., methyl, ethyl, n-propyl, i-propyl, n-butyl, i-butyl, s-butyl, t-butyl, n-pentyl, 1-methylbutyl, 2-methylbutyl, 3-methylbutyl, neopentyl, 3,3-dimethylpropyl, hexyl, 2-methylpentyl, and the like). Similarly, the alkyl portion (i.e., alkyl moiety) of an alkoxy, acyl (e.g., alkanoyl), alkylamino, dialkylamino, and alkylthio group has the same definition as above.

The term "cycloalkyl" refers to a nonaromatic carbocyclic ring that is fully hydrogenated and exists as a monocyclic ring. Unless specified otherwise, the carbocyclic ring is generally a 3- to 8-membered ring. For example, a fully saturated cycloalkyl include groups such as cyclopropyl, cyclobutyl, cyclopentyl, cyclohexyl, and the like.

The term "heteroaryl" refers to an aromatic ring structure containing from 5 to 14 ring atoms in which at least one of the ring atoms is a heteroatom (i.e., oxygen, nitrogen, or sulfur), with the remaining ring atoms being independently selected from the group consisting of carbon, oxygen, nitrogen, and sulfur. A heteroaryl may be a single ring or 2 or 3 fused rings. Examples of heteroaryl substituents include 6-membered ring substituents such as pyridyl, pyrazyl, pyrimidinyl, and pyridazinyl; 5-membered ring substituents such as triazolyl, imidazolyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as benzothiofuranyl, isobenzothiofuranyl, benzisoxazolyl, benzoxazolyl, purinyl, and anthranilyl; and 6/6-membered fused rings such as quinolinyl, isoquinolinyl, cinnolinyl, quinazolinyl, and 1,4-benzoxazinyl. In a group that has a heteroaryl substituent, the ring atom of the heteroaryl substituent that is bound to the group may be the at least one heteroatom, or it may be a ring carbon atom, where the ring carbon atom may be in the same ring as the at least one heteroatom or where the ring carbon atom may be in a different ring from the at least one heteroatom. Similarly, if the heteroaryl substituent is in turn substituted with a group or substituent, the group or substituent may be bound to the at least one heteroatom, or it may be bound to a ring carbon atom, where the ring carbon atom may be in the same ring as the at least one heteroatom or where the ring carbon atom may be in a different ring from the at least one heteroatom. The term "heteroaryl" also includes pyridyl N-oxides and groups containing a pyridine N-oxide ring.

Examples of single-ring heteroaryls include furanyl, dihydrofuranyl, tetradydrofuranyl, thiophenyl (also known as "thiofuranyl"), dihydrothiophenyl, tetrahydrothiophenyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiaediazolyl, oxathiazolyl, oxadiazolyl (including oxadiazolyl, 1,2,4-oxadiazolyl (also known as "azoximyl"), 1,2,5-oxadiazolyl (also known as "furazanyl"), or 1,3,4-oxadiazolyl), oxatriazolyl (including 1,2,3,4-oxatriazolyl or 1,2,3,5-oxatriazolyl), dioxazolyl (including 1,2,3-dioxazolyl, 1,2,4-dioxazolyl, 1,3,2-dioxazolyl, or 1,3,4-dioxazolyl), oxathiazolyl, oxathiolyl, oxathiolanyl, pyranyl (including 1,2-pyranyl or 1,4-pyranyl), dihydropyranyl, pyridinyl (also known as "azinyl"), piperidinyl, diazinyl (including pyridazinyl (also known as "1,2-diazinyl"), pyrimidinyl (also known as "1,3-diazinyl" or "pyrimidyl"), or pyrazinyl (also known as "1,4-diazinyl")), piperazinyl, triazinyl (including s-triazinyl (also known as "1,3,5-triazinyl"), as-triazinyl (also known 1,2,4-triazinyl), and v-triazinyl (also known as "1,2,3-triazinyl")), oxazinyl (including 1,2,3-oxazinyl, 1,3,2-oxazinyl, 1,3,6-oxazinyl (also known as "pentoxazolyl"), 1,2,6-oxazinyl, or 1,4-oxazinyl), isoxazinyl (including o-isoxazinyl or p-isoxazinyl), oxazolidinyl, isoxazolidinyl, oxathiazinyl (including 1,2,5-oxathiazinyl or 1,2,6-oxathiazinyl), oxadiazinyl (including 1,4,2-oxadiazinyl or 1,3,5,2-oxadiazinyl), morpholinyl, azepinyl, oxepinyl, thiepinyl, and diazepinyl.

Examples of 2-fused-ring heteroaryls include, indolizinyl, pyrindinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl, indolyl, isoindolyl, indoleninyl, isoindazolyl, benzazinyl, phthalazinyl, quinoxalinyl, quinazolinyl, benzodiazinyl, benzopyranyl, benzothiopyranyl, benzoxazolyl, indoxazinyl, anthranilyl, benzodioxolyl, benzodioxanyl, benzoxadiazolyl, benzofuranyl, isobenzofuranyl, benzothienyl, isobenzothienyl, benzothiazolyl, benzothiadiazolyl, benzimidazolyl, benzotriazolyl, benzoxazinyl, benzisoxazinyl, and tetrahydroisoquinolinyl.

Examples of 3-fused-ring heteroaryls or heterocycloalkyls include 5,6-dihydro-4H-imidazo[4,5,1-ij]quinoline, 4,5-dihydroimidazo[4,5,1-hi]indole, 4,5,6,7-tetrahydroimidazo[4,5,1-jk][1]benzazepine, and dibenzofuranyl.

Other examples of fused-ring heteroaryls include benzo-fused heteroaryls such as indolyl, isoindolyl (also known as "isobenzazolyl" or "pseudoisoindolyl"), indoleninyl (also known as "pseudoindolyl"), isoindazolyl (also known as "benzpyrazolyl"), benzazinyl (including quinolinyl (also known as "1-benzazinyl") or isoquinolinyl (also known as "2-benzazinyl")), phthalazinyl, quinoxalinyl, quinazolinyl, benzodiazinyl (including cinnolinyl (also known as "1,2-benzodiazinyl") or quinazolinyl (also known as "1,3-benzodiazinyl")), benzopyranyl (including "chromanyl" or "isochromanyl"), benzothiopyranyl (also known as "thiochromanyl"), benzoxazolyl, indoxazinyl (also known as "benzisoxazolyl"), anthranilyl, benzodioxolyl, benzodioxanyl, benzoxadiazolyl, benzofuranyl (also known as "coumaronyl"), isobenzofuranyl, benzothienyl (also known as "benzothiophenyl," "thionaphthenyl," or "benzothiofuranyl"), isobenzothienyl (also known as "isobenzothiophenyl," "isothionaphthenyl," or "isobenzothiofuranyl"), benzothiazolyl, benzothiadiazolyl, benzimidazolyl, benzotriazolyl, benzoxazinyl (including 1,3,2-benzoxazinyl, 1,4,2-benzoxazinyl, 2,3,1-benzoxazinyl, or 3,1,4-benzoxazinyl), benzisoxazinyl (including 1,2-benzisoxazinyl or 1,4-benzisoxazinyl), tetrahydroisoquinolinyl, carbazolyl, xanthenyl, and acridinyl.

The term "heterocycle" refers to a saturated or partially saturated ring structure containing a total of 3 to 14 ring atoms. At least one of the ring atoms is a heteroatom (i.e., oxygen, nitrogen, or sulfur), with the remaining ring atoms being independently selected from the group consisting of carbon, oxygen, nitrogen, and sulfur. A heterocycle alternatively may comprise 2 or 3 rings fused together, wherein at least one such ring contains a heteroatom as a ring atom (e.g., nitrogen, oxygen, or sulfur). In a group that has a heterocycle substituent, the ring atom of the heterocycle substituent that is bound to the group may be the at least one heteroatom, or it may be a ring carbon atom, where the ring carbon atom may be in the same ring as the at least one heteroatom or where the ring carbon atom may be in a different ring from the at least one heteroatom. Similarly, if the heterocycle substituent is in turn substituted with a group or substituent, the group or substituent may be bound to the at least one heteroatom, or it may be bound to a ring carbon atom, where the ring carbon atom may be in the same ring as the at least one heteroatom or where the ring carbon atom may be in a different ring from the at least one heteroatom.

The term "organic cation" refers to a positively charged organic ion. The exemplary organic cations include ammonium cations unsubstituted or substituted with alkyl or cycloalkyl group.

The term "inorganic cation" refers to a positively charged metal ion. The exemplary inorganic cations include Group I metal cations such as sodium, potassium, magnesium, calcium and the like.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. The term "animal" refers to humans (male or female), companion animals (e.g., dogs, cats and horses), zoo animals, marine animals, birds and other similar animal species.

As used herein, a subject is "in need of" a treatment if such subject would benefit biologically, medically or in quality of life from such treatment (preferably, a human).

The phrase "pharmaceutically acceptable" indicates that the substance or composition must be compatible chemically and/or toxicologically, with the other ingredients comprising a formulation, and/or the mammal being treated therewith.

The term "compounds of the present invention" (unless specifically identified otherwise) refer to compounds of Formula (I) and salts thereof, as well as all stereoisomers (including diastereoisomers and enantiomers), rotamers, tautomers and isotopically labeled compounds (including deuterium substitutions), as well as inherently formed moieties (e.g., polymorphs, solvates and/or hydrates). For purposes of this invention, solvates and hydrates are generally considered compositions.

DETAILED DESCRIPTION

The present invention provides compounds and pharmaceutical formulations thereof that are useful in the treatment tuberculosis, in particular MDR or XDR resistant tuberculosis.

Compounds of the present invention may be synthesized by synthetic routes that include processes analogous to those well-known to those of skill in the art, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, Reagents for Organic Synthesis, v. 1-19, Wiley, New York (1967-1999 ed.), or Beilsteins Handbuch der organischen Chemie, 4, Aufl. ed. Springer-Verlag, Berlin, including supplements (also available via the Beilstein online database)).

For illustrative purposes, the reaction schemes depicted in Examples section provide potential routes for synthesizing the compounds of the present invention as well as key intermediates. The Examples section also provides a more detailed description of the individual reaction steps. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the present invention, protection of remote functionality (e.g., primary or secondary amino, or carboxyl groups) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). Suitable carboxyl protecting groups (C(O)O-Pg) include alkyl esters (e.g., methyl, ethyl or t-butyl), benzyl esters, silyl esters, and the like. The need for such protection is readily determined by one skilled in the art. For a general description of protecting groups and their use, see T. W. Greene, Protective Groups in Organic Synthesis, John Wiley & Sons, New York, 1991.

The compounds and intermediates may be isolated and used as the compound per se or as its salt. As used herein, the terms "salt" or "salts" refers to an acid addition or base addition salt of a compound of the invention or intermediate. "Salts" include in particular "pharmaceutical acceptable salts". The term "pharmaceutically acceptable salts" refers to salts that retain the biological effectiveness and properties of the compounds of this invention and, which typically are not biologically or otherwise undesirable.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfornate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorus, fluorine, and chlorine, such as $^{2}H$, $^{3}H$, $^{11}C$, $^{13}C$, $^{14}C$, $^{15}N$, $^{18}$F $^{31}$P, $^{32}$P, $^{35}$S, $^{36}$Cl, $^{125}$I respectively. The invention includes various isotopically labeled compounds as defined herein, for example those into which radioactive isotopes, such as $^3$H, $^{13}$C, and $^{14}$C, are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically labeled compounds of this invention can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^2$H or D) may afford certain therapeutic advantages resulting from greater metabolic stability, for example increased in vivo half-life, reduced dosage requirements, reduced cyp inhibition (competitive or time dependent) or an improvement in therapeutic index. For example, substitution with deuterium may modulate undesirable side effects of the undeuterated compound, such as competitive cyp inhibition, time dependent cyp inactivation, etc. It is understood that deuterium in this context is regarded as a substituent in compounds of the present invention (including both the monomeric and linker moieties of the dimer). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-labeled compounds of the present invention can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

It will be recognized by those skilled in the art that the compounds of the present invention may contain chiral centers and as such may exist in different isomeric forms. As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound.

"Enantiomers" are a pair of stereoisomers that are non-superimposable mirror images of each other. A 1:1 mixture of a pair of enantiomers is a "racemic" mixture. The term is used to designate a racemic mixture where appropriate.

"Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S)-.

Unless specified otherwise, the compounds of the present invention are meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Compounds of the invention that contain groups capable of acting as donors and/or acceptors for hydrogen bonds may be capable of forming co-crystals with suitable co-crystal formers. These co-crystals may be prepared from compounds of the present invention by known co-crystal forming procedures. Such procedures include grinding, heating, co-subliming, co-melting, or contacting in solution compounds of the present invention with the co-crystal former under crystallization conditions and isolating co-crystals thereby formed. Suitable co-crystal formers include those described in WO 2004/078163. Hence the invention further provides co-crystals comprising a compound of the present invention.

The compounds of the present invention are typically used as a pharmaceutical composition (e.g., a compound of the present invention and at least one pharmaceutically acceptable carrier). As used herein, the term "pharmaceutically acceptable carrier" includes generally recognized as safe (GRAS) solvents, dispersion media, surfactants, antioxidants, preservatives (e.g., antibacterial agents, antifungal agents), isotonic agents, salts, preservatives, drug stabilizers, buffering agents (e.g., maleic acid, tartaric acid, lactic acid, citric acid, acetic acid, sodium bicarbonate, sodium phosphate, and the like), and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated. For purposes of this invention, solvates and hydrates are considered pharmaceutical compositions comprising a compound of the present invention and a solvent (i.e., solvate) or water (i.e., hydrate).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. The compound of the present invention is typically formulated into pharmaceutical dosage forms to provide an easily controllable dosage of the drug and to give the patient an elegant and easily handleable product.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

In certain instances, it may be advantageous to administer the compound of the present invention in combination with at least one additional pharmaceutical (or therapeutic) agent (e.g., first-line or second-line antituberculosis drugs, and for patients with HIV or AIDS an HIV/AIDS drug). The compound of the present invention may be administered either simultaneously with, or before or after, one or more other therapeutic agent(s). Alternatively, the compound of the present invention may be administered separately, by the same or different route of administration, or together in the same pharmaceutical composition as the other agent(s).

Suitable additional TB agents include first-line drugs (such as isoniazid, rifampicin, pyrazinamide, ethambutol and combinations thereof); second-line drugs (such as streptomycin, kanamycin, amikacin, capreomycin, ofloxacin, levofloxacin, moxifloxacin, cycloserine, para-aminosalicylic add, ethioamide, prothionamide, thioacetazone and combinations thereof); and other antituberculosis drugs (such as clofazimine, amoxicilin with clavulanate, imipenem, linezolid, clarithromycin, thioridazine and combinations thereof).

Other potential additional TB agents include compounds such as bicyclic nitroimidazoles (e.g., (S)-6,7-dihydro-2-nitro-6-[[4-(trifluoromethoxy)phenyl]methoxy]-5H-imidazo[2,1-b][1,3]oxazine (PA-824) and TBA-354, available from TB Alliance), bedaquiline (TMC-207), delamanid (OPC67683), oxazolidinone, 2-[(2S)-2-methyl-1,4-dioxa-8-azaspiro[4.5]decan-8-yl]-8-nitro-6-trifluoromethyl-4H-1,3-benzothiazin-4-one (BTZ043), imidazopyridines (e.g., Q201, available from Quro Science Inc.), and combinations thereof.

Suitable therapeutic agents for adjunct therapy include human immunodeficiency virus (HIV) drugs, immunotherapeutic agents, (e.g., anti-interleukin 4 neutralizing antibodies, *mycobacterium vaccae*, high-dose intravenous immunoglobulin, 16a-bromoepiandosterone (HE2000), RUTI® vaccine, DNA vaccine with HSP65, Ag85, MPT-64, and MPT-83, dzherelo (plant extracts from the Ukraine), cytokines (such as Interleukin 2, Interleukin 7, Interleukin 15, Interleukin 27, Interleukin 12, Interferon γ), immunosuppressive agents (such as corticosteroids, thalidomide, and etanercept)), steroids, anti-inflammatory agents (e.g., prednisone), and other agents well-known to those of skill in art for use in improving the quality of care for patients being treated for the diseases, conditions, or disorders described herein.

Suitable HIV/AIDS drugs include non-nucleoside reverse transcriptase inhibitors (NNRTIs), such as efavirenz (Sustiva), etravirine (Intelence) and nevirapine (Viramune); Nucleoside reverse transcriptase inhibitors (NRTIs), such as Abacavir (Ziagen), and the combination drugs emtricitabine and tenofovir (Truvada), and lamivudine and zidovudine (Combivir); Protease inhibitors (PIs), such as atazanavir (Reyataz), darunavir (Prezista), fosamprenavir (Lexiva) and ritonavir (Norvir); Entry or fusion inhibitors, such enfuvirtide (Fuzeon) and maraviroc (Selzentry); and Integrase inhibitors, such as Raltegravir (Isentress).

The compound of the present invention or pharmaceutical composition thereof for use in humans is typically administered orally at a therapeutic dose.

The typical dose (effect amount) range is generally from about 100 mg to about 1100 mg/day to a 70 kg body weight adult for full treatment duration in an acceptable formulation. The "effective amount" of a compound of the invention is the amount necessary or sufficient to treat or prevent a disease caused by a mycobacterial infections such as those caused by *Mycobacterium tuberculosis, Mycobacterium bovis, Mycobacterium leprae, Mycobacterium africanum, Mycobacterium avium, Mycobacterium microti*, or any *mycobacterium* that causes multi-drug resistant (MDR) TB or extensively resistant (XDR) TB, or any other mycobacterial species known to cause disease in humans. The effective amount can vary depending on the compound employed, the mode of administration, the treatment desired and the disease indicated, as well as other factors such as a patient's age, body weight, general health and sex. Furthermore, several divided dosages, as well as staggered dosages, can be administered daily or sequentially, or the dose can be continuously infused, or can be a bolus injection. Further, the dosages of the compounds of the invention can be proportionally increased or decreased as indicated by the exigencies of the therapeutic or prophylactic situation.

In general, the therapeutically effective dosage of a compound, the pharmaceutical composition, or the combinations thereof, is dependent on the species of the subject, the body weight, age and individual condition, the disorder or disease or the severity thereof being treated. A physician, pharmacist, clinician or veterinarian of ordinary skill can readily determine the effective amount of each of the active ingredients necessary to prevent, treat or inhibit the progress of the disorder or disease.

The International Standards for Tuberculosis Care describes a widely accepted level of care that all practitioners, public and private, should follow in dealing with people who have, or are suspected of having, tuberculosis. The Standards are intended to facilitate the effective engagement of all care providers in delivering high-quality care for patients of all ages, including those with sputum smear-positive, sputum smear-negative, and extrapulmonary tuberculosis; tuberculosis caused by drug resistant *Mycobacterium tuberculosis* complex (*M. tuberculosis*) organisms; and tuberculosis combined with human immunodeficiency virus (HIV) infection.

Another aspect of the invention is a product comprising a compound of the present invention and at least one other therapeutic agent (or pharmaceutical agent) as a combined preparation for simultaneous, separate or sequential use in therapy to treat a subject having sputum smear-positive, sputum smear-negative, and extrapulmonary tuberculosis; tuberculosis caused by drug resistant *Mycobacterium tuberculosis* complex (*M. tuberculosis*) organisms; or tuberculosis combined with human immunodeficiency virus (HIV) infection.

In the combination therapies of the invention, the compound of the present invention and the other therapeutic agent may be manufactured and/or formulated by the same or different manufacturers. Moreover, the compound of the present invention and the other therapeutic (or pharmaceutical agent) may be brought together into a combination therapy: (i) prior to release of the combination product to physicians (e.g. in the case of a kit comprising the compound of the invention and the other therapeutic agent or fixed dose composition); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of the present invention for treating tuberculosis, in particular MDR and XDR resistant tuberculosis, wherein the medicament is prepared for administration with another therapeutic agent. The invention also provides for the use of another therapeutic agent, wherein the medicament is administered as a combination of a compound of the present invention with the other therapeutic agent.

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

EXAMPLES

Unless specified otherwise, starting materials are generally available from commercial sources such as TCI Fine Chemicals (Japan), Shanghai Chemhere Co., Ltd. (Shanghai, China), Aurora Fine Chemicals LLC (San Diego, Calif.), FCH Group (Ukraine), Aldrich Chemicals Co. (Milwaukee, Wis.), Lancaster Synthesis, Inc. (Windham, N.H.), Acros Organics (Fairlawn, N.J.), Maybridge Chemical Company, Ltd. (Cornwall, England), Tyger Scientific (Princeton, N.J.), AstraZeneca Pharmaceuticals (London, England), Chembridge Corporation (USA), Matrix Scientific (USA), Conier Chem & Pharm Co., Ltd (China), Enamine Ltd (Ukraine), Combi-Blocks, Inc. (San Diego, USA), Oakwood Products, Inc. (USA), Apollo Scientific Ltd. (UK), Allichem LLC. (USA) and Ukrorgsyntez Ltd (Latvia), Johnson Matthey Chemicals (India), Fluorochem (UK)

The following abbreviations used herein below have the corresponding meanings:

h hour(s)
rt room temperature
aq. aqueous
sat. saturated
$Cs_2CO_3$ cesium carbonate
DCM dichloromethane
NMR nuclear magnetic resonance
MS mass spectrometry
HPLC high performance liquid chromatography
DMSO dimethylsulfoxide
MeOH methanol
EtOH ethanol
EtOAc ethyl acetate
MeCN acetonitrile
DMF dimethylformamide
THF tetrahydrofuran
NaH sodium hydride
$Na_2SO_4$ sodium sulfate
NaOH sodium hydroxide
$NaHCO_3$ sodium bicarbonate
$NH_4OH$ ammonium hydroxide
HCl hydrochloric acid
DMAP 4-dimethylaminopyridine
$KHSO_4$ potassium bisulfate
$(COCl)_2$ oxalyl chloride
MeI methyl Iodide
NaOMe sodium methoxide
$K_2CO_3$ potassium carbonate
TBAI tetra-n-butylammonium iodide
DIPEA N,N-diisopropylethylamine
$SOCl_2$ thionyl chloride
$PCl_5$ phosphorus pentachloride
$NH_3$ ammonia
NBS N-bromosuccinimide
BnBr benzyl bromide
$Ag_2CO_3$ silver carbonate
$Ac_2O$ acetic anhydride
$BBr_3$ boron tribromide
$Pd(PPh_3)_2Cl_2$ bis(triphenylphosphine)palladium(II) dichloride General Procedures Schemes 1-7 (below), as illustrated in Methods 1-5, describe potential routes for producing compounds of Formula (I).

Method-1:

Scheme 1 as illustrated in Method-1 can be used for the synthesis of 4-substituted ethyl 3-aminobut-2-enoate from corresponding acids or acid chlorides according to procedures described in US007396936B1

Scheme 1

Oxalyl chloride (3 equiv.) was added to a solution of acid (1 equiv.) in DCM and stirred overnight at rt. After evaporation under reduced pressure and drying in high vacuum, the crude chloride (1 equiv.) was added to a mixture of 2,2-dimethyl-1,3-dioxane-4,6-dione (1.1 equiv.) and DMAP (1 equiv.) in DCM at 0° C. The reaction mixture was stirred at rt for 2.5 h. The reaction mixture was quenched by aq $KHSO_4$ and extracted with DCM. The organic layer was washed with aq $KHSO_4$ solution, brine, dried over anhydrous $Na_2SO_4$ and concentrated in vacuo. The crude compound was purified by column chromatography over silica gel (100-200 mesh) using a solvent gradient of EtOAc in pet ether as eluent to afford 5-(substituted-1-hydroxyethylidene)-2,2-dimethyl-1,3-dioxane-4,6-dione which was dissolved in EtOH and refluxed for 6 h. The reaction mixture was evaporated in vacuo and dried under high vacuum. To the crude ethyl 4-substituted 3-hydroxybut-2-enoate (1 equiv.) in EtOH was added 25% of NH₄OH solution (1 mL/6 mmol) and the resulting solution was stirred at rt. The reaction mixture was concentrated under reduced pressure and the desired compound was isolated by column chromatography over silica gel (100-200 mesh) using a solvent gradient of EtOAc in pet ether as eluent to afford 4-substituted ethyl 3-aminobut-2-enoate and the byproduct amide.

Method-2:

Scheme 2 as illustrated in Method-2 can be used for the synthesis of 2-substituted aryl malonates from diethyl malonate according to procedures described in Org. Lett. 9, 3469-3472 (2007).

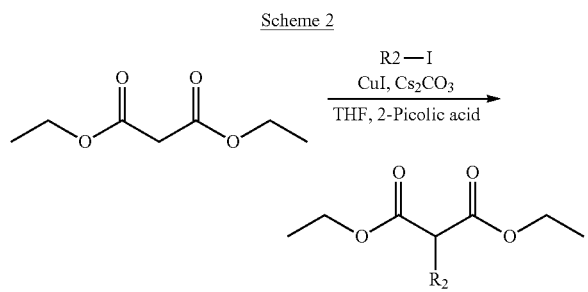

To a solution of aryl iodide (1 equiv.) in THF (5 mL/mmol) were added diethylmalonate (2 equiv.), CuI (0.05 equiv.) 2-picolinic acid (0.2 equiv.) or 2-hydroxybiphenyl, followed by Cs₂CO₃ (1.5 equiv.) and refluxed at 80° C. The resulting reaction mixture was quenched with saturated aq NH₄Cl and the product was extracted with EtOAc. The combined extracts were washed with brine, dried over anhydrous Na₂SO₄ and concentrated in vacuo. The crude product was purified by column chromatography on silica gel (100-200 mesh) using a solvent gradient of EtOAc in pet ether as eluent to afford 2-substituted aryl malonates.

Method-3A:

Scheme 3 as illustrated in Method-3A can be used for the synthesis of substituted pyridones from corresponding 4-substituted ethyl 3-aminobut-2-enoate and 2-substituted malonates according to procedures described in Eur. J. Med. Chem. 26, 599-604 (1991).

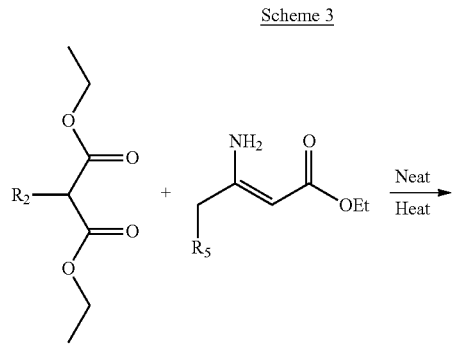

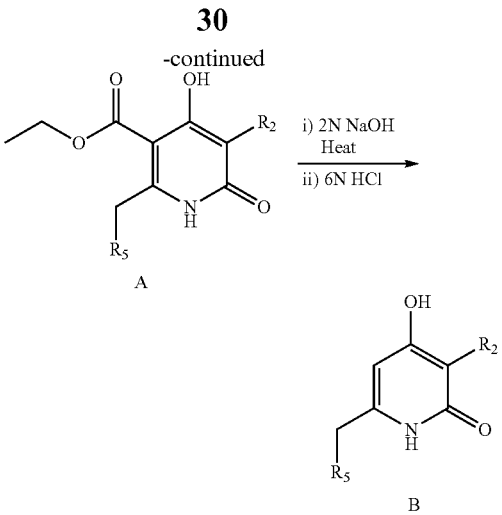

A mixture of 4-substituted ethyl 3-aminobut-2-enoate (1 eq.) and 2-substituted malonates (1 eq.) was heated neat at 220° C. for 45 minutes. Consumption of starting materials and the formation of intermediate A was monitored by LC-MS. The residue was then dissolved in 2N NaOH solution and the resultant mixture was heated in a Biotage microwave reactor at 160° C. for 1 h. Conversion of intermediate A to desired product B was monitored by LC-MS. The reaction mixture was cooled and acidified with 6N HCl solution. The precipitated solids were collected and dried in vacuo. The crude substituted pyridone was dissolved in DMSO and purified by reverse-phase HPLC.

Method-3B:

Scheme 4 as illustrated in Method-3B can be used for the synthesis of substituted pyridones from corresponding 4-substituted ethyl 3-aminobut-2-enoate and 2-substituted malonates according to procedures described in Eur. J. Med. Chem. 26, 599-604 (1991).

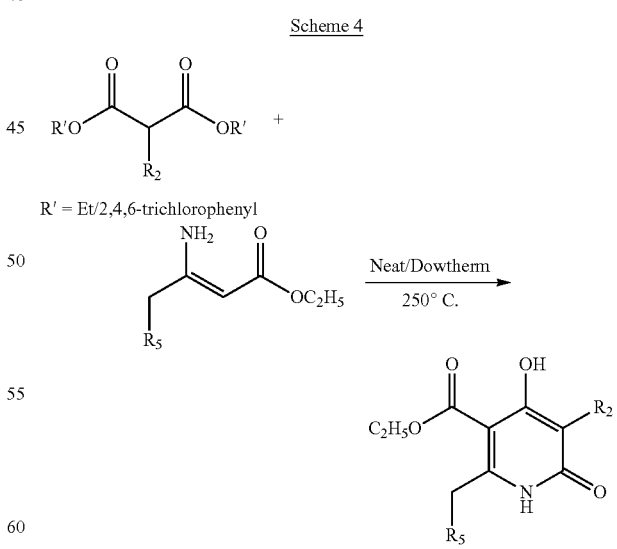

A mixture of s 2-substituted malonates (1 eq.) and 4-substituted ethyl 3-aminobut-2-enoate (1 eq.) as a neat or in dowtherm or in diphenylether was heated up to 250° C. The resulting reaction mixture was cooled to rt and pet ether or 25% diethyl ether in petroleum ether was added to reaction mixture. The solid was washed with pentane and dried to afford substituted pyridones as a solid.

Method-3C

Scheme 5 as illustrated in Method-3C can be used for the synthesis of substituted pyridones from corresponding 4-substituted ethyl 3-aminobut-2-enoate and 2-substituted malonates according to procedures described in Eur. J. Med. Chem. 26, 599-604 (1991).

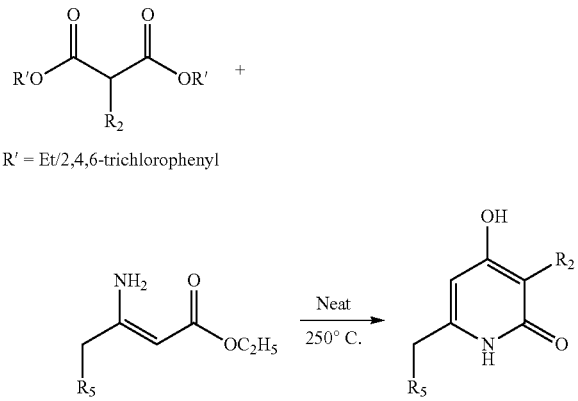

Scheme 5

R' = Et/2,4,6-trichlorophenyl

A mixture of 2-substituted malonates (1 eq.) and 4-substituted ethyl 3-aminobut-2-enoate (1 eq.) as a neat or in dowtherm or in diphenyl ether was heated up to 250° C. The resulting reaction mixture was cooled to rt and pet ether or 25% diethyl ether in petroleum ether was added to reaction mixture. The solid was washed with pentane and dried to afford substituted pyridones as a solid.

Method-4:

Scheme 6 as illustrated in Method-4 (including 4A and 4B) can be used for decarboxylation of substituted pyridones according to procedures described in Eur. J. Med. Chem. 26, 599-604 (1991).

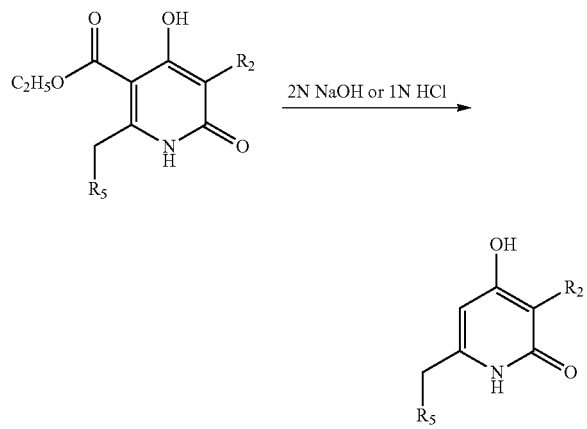

Scheme 6

Method-4A (Decarboxylation Under Basic Condition):

A solution of ethyl 4-hydroxy-2,5-disubstituted-6-oxo-1,6-dihydropyridine-3-carboxylate in aq. 2N NaOH solution was maintained at 130° C. up to 24 h. The reaction mass was cooled to rt and acidified with 1N HCl. Solid formed was filtered, washed with petroleum ether and dried to afford 4-hydroxy-3,6-disubstitutedpyridin-2(1H)-one as an off-white solid (in instances where precipitation was not observed, reaction mixture was extracted with EtOAc, the combined organic layer was washed with water, 5% aq sodium bicarbonate, brine, dried over anhydrous $Na_2SO_4$ and concentrated to afford 4-hydroxy-3,6-disubstitutedpyridin-2(1H)-one as a solid.

Method-4B (Decarboxylation Under Acidic Condition):

Ethyl 4-hydroxy-2,5-disubstituted-6-oxo-1,6-dihydropyridine-3-carboxylate and 2N HCl was maintained at 130° C. up to 24 h. The reaction mass was cooled to rt and neutralized with aq saturated $NaHCO_3$. The solid was collected by filtration, washed with pet ether and dried to afford 4-hydroxy-3,6-disubstitutedpyridin-2(1H)-one. In instances where precipitation was not observed, reaction mixture was extracted with EtOAc. The combined organic layer was washed with water, 5% aq sodium bicarbonate, brine, dried over anhydrous $Na_2SO_4$ and concentrated to afford 4-hydroxy-3,6-disubstitutedpyridin-2(1H)-one as a solid.

Method-5:

Scheme 7 as illustrated in Method-5 can be used for the synthesis of bis(2,4,6-trichlorophenyl) 2-substituted malonates from 2-substituted malonic acid according to procedures described in PCT Publication No. WO2009/099929 A1

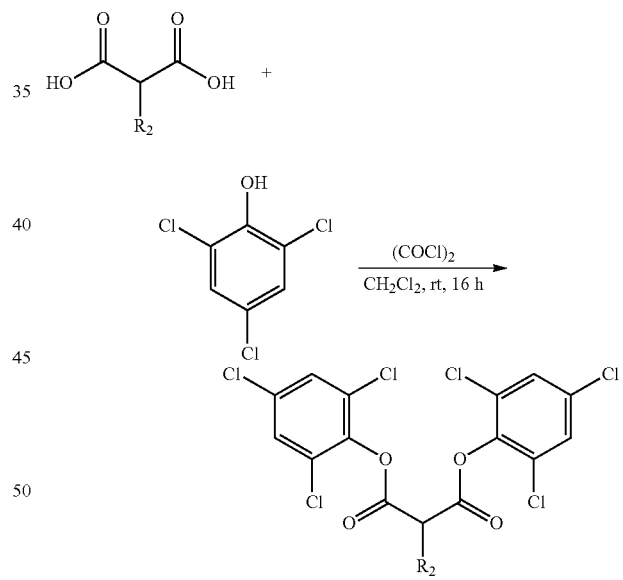

Scheme 7

To a solution of 2-substituted malonic acid (1 equiv.) in DCM at 0° C. was added oxalyl chloride (2.6 equiv.) and stirred well at rt for 1 h. Then 2,4,6-trichlorophenol (2.7 equiv.) was added and the resulting reaction mixture was stirred at rt for 16 h. The reaction mixture was concentrated and the residue obtained was diluted with MeOH. The precipitated solid was collected by filtration and dried to afford bis(2,4,6-trichlorophenyl) 2-substituted malonates.

Preparation of Key Intermediates

The following 4-substituted ethyl 3-aminobut-2-enoates were prepared according to the Method-1 using corresponding commercially available acids (see Scheme 1). Commercially not available (4,4-dimethylcyclohexyl)acetic acid was prepared using reported procedure in US2004/0077618 A1 and (4,4-difluorocyclohexyl)acetic acid was prepared according to procedure reported in Tetrahedron 51, 10259-10280 (1995) and US2006/264489.

Preparation of ethyl 4-(4,4-dimethylcyclohexyl)-3-oxobutanoate

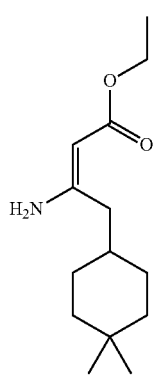

Step-1: preparation of ethyl 2-(4,4-dimethylcyclohex-2-enylidene)acetate

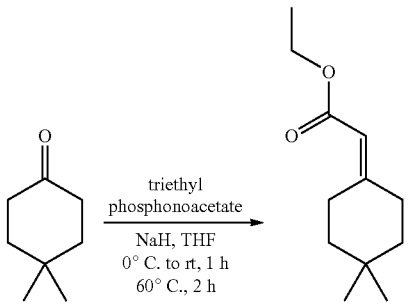

To a solution of NaH (38.02 g, 0.990 mol, 60% in oil) in THF (1.5 L) at 0° C. was added triethyl phosphonoacetate (157.2 mL, 0.792 mol) and the mixture stirred well at rt for 1 h. Then 4,4-dimethylcyclohexanone (100 g, 0.792 mol) was added and the mixture stirred well at 60° C. for 2 h. The reaction mixture was quenched with ice cold sat aq NH$_4$Cl solution (1 L) and the product was extracted with EtOAc (3×350 mL). The combined organic layer was washed with brine (3×150 mL), dried over anhydrous Na$_2$SO$_4$ and concentrated under reduced pressure to afford crude 170 g of ethyl 2-(4,4-dimethylcyclohexylidene)acetate as a pale yellow liquid. It was used as such in next step without further purification.

$^1$H NMR: (400 MHz, CDCl$_3$): δ 5.50 (s, 1H), 4.16 (q, J=7.6 Hz, 2H), 2.10-1.95 (br s, 2H), 1.90-1.80 (br s, 2H), 1.50-1.30 (m, 7H), 0.90 (s, 6H).

Step-2: Preparation of Ethyl 2-(4,4-dimethylcyclohexyl)acetate

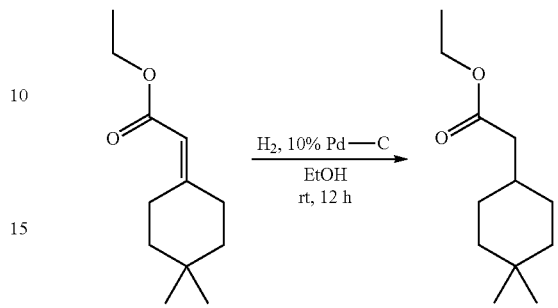

To a solution of ethyl 2-(4,4-dimethylcyclohexylidene)acetate (155 g, 789.64 mmol) in EtOH (1.2 L) was added 10% Pd/C (13.0 g) and hydrogenated at 50 psi hydrogen pressure for 12 h. The reaction mixture was filtered through Celite and concentrated to afford 150 g (96%, two steps) of ethyl 2-(4,4-dimethylcyclohexyl)acetate as a pale yellow liquid.

$^1$H NMR: (400 MHz, CDCl$_3$): δ 4.12 (q, J=7.2 Hz, 2H), 2.19 (d, J=7.2 Hz, 2H), 1.80-1.60 (m, 1H), 1.60-1.50 (m, 2H), 1.40-1.10 (m, 9H), 0.89 (s, 3H), 0.86 (s, 3H).

Step-3: Preparation of 2-(4,4-Dimethylcyclohexyl)acetic acid

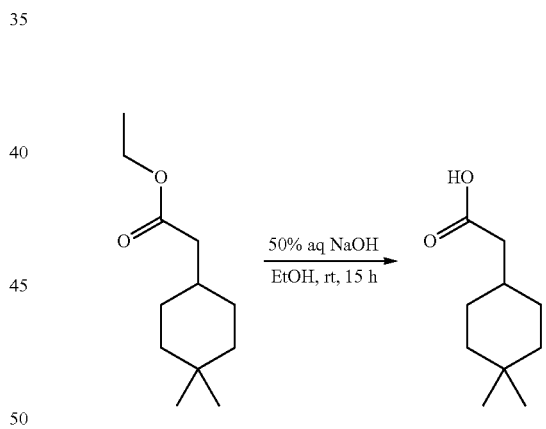

To a solution of ethyl 2-(4,4-dimethylcyclohexyl)acetate (150 g, 756.42 mmol) was added 50% aq. NaOH (800 mL) in absolute EtOH (800 mL) and stirred at rt for 15 h. It was washed with ether (3×120 mL) to remove impurities. Then the reaction mixture was acidified to pH 2 using 2N aq. HCl solution and the product was extracted with EtOAc (3×350 mL). The combined organic layer was washed with brine (3×150 mL), dried over anhydrous Na$_2$SO$_4$ and concentrated under reduced pressure to afford 120 g (93%) of 2-(4,4-dimethylcyclohexyl)acetic acid as a viscous liquid.

$^1$H NMR: (400 MHz, DMSO-d$_6$): δ 11.98 (s, 1H), 2.10 (d, J=6.4 Hz, 2H), 1.60-1.40 (m, 3H), 1.40-1.25 (m, 2H), 1.20-1.05 (m, 4H), 0.87 (s, 3H), 0.84 (s, 3H).

Step-4: Preparation of 5-(2-cyclohexyl-1-hydroxy-ethylidene)-2,2-dimethyl-1,3-dioxane-4,6-dione

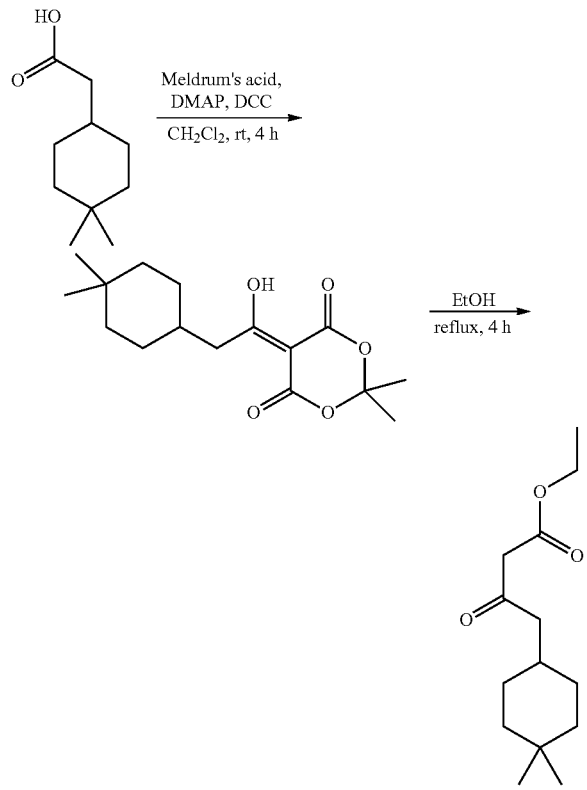

To a solution of 2-(4,4-dimethylcyclohexyl)acetic acid (120 g, 0.704 mol) in DCM (1.2 L) at 0° C. were added Meldrum's acid (132.2 g, 0.92 mol) and DMAP (129.1 g, 1.06 mol) followed by DCC (218.1 g, 1.06 mol) and the mixture stirred well at rt for 4 h. The reaction mixture was diluted with DCM (500 mL), washed with 10% aq. citric acid (3×150 mL) followed by water (3×150 mL), brine (3×150 mL) and concentrated to get 100 g of crude 5-(2-cyclohexyl-1-hydroxyethylidene)-2,2-dimethyl-1,3-dioxane-4,6-dione as colorless liquid. The crude 5-(2-cyclohexyl-1-hydroxyethylidene)-2,2-dimethyl-1,3-dioxane-4,6-dione (100 g) was dissolved in EtOH (700 mL) and refluxed for 4 h. The reaction mixture was concentrated under reduced pressure. The crude compound was purified by 100-200 silica using 15-20% EtOAc in Hexanes as eluent to give 90 g (53%) of pure ethyl 4-(4,4-dimethylcyclohexyl)-3-oxobutanoate as a colorless liquid.

$^1$H NMR (400 MHz, CDCl$_3$): δ 4.18 (q, J=7.2 Hz, 2H), 3.41 (s, 2H), 2.44 (d, J=6.8 Hz, 2H), 1.80-1.70 (m, 1H), 1.56-1.48 (m, 2H), 1.40-1.05 (m, 9H), 0.89 (s, 3H), 0.85 (s, 3H).

Step-5: Preparation of Ethyl 3-amino-4-(4,4-dimethylcyclohexyl)but-2-enoate

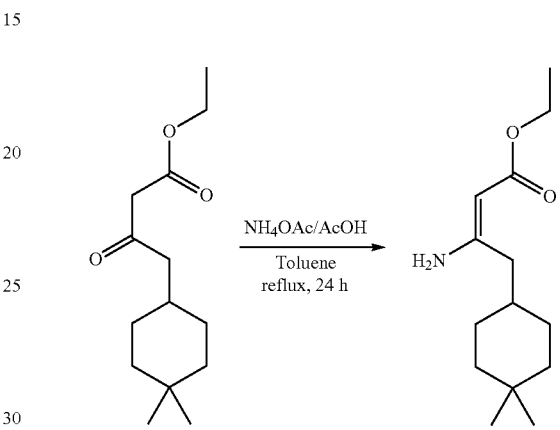

To a solution of ethyl 4-(4,4-dimethylcyclohexyl)-3-oxobutanoate (90 g, 644.5 mmol) in toluene (750 mL) were added ammonium acetate (144.3 g, 1.87 mol), AcOH (21.4 mL, 374.5 mmol) and the mixture refluxed using Dean-Stork apparatus for 36 h. The reaction mixture was concentrated under reduced pressure to afford 75 g (84%) of ethyl 3-amino-4-(4,4-dimethylcyclohexyl)but-2-enoate as a colorless liquid.

$^1$H NMR (400 MHz, CDCl$_3$): δ 4.51 (s, 1H), 4.15 (q, J=6.8 Hz, 2H), 2.08-1.98 (m, 2H), 1.60-1.54 (m, 2H), 1.50-1.34 (m, 3H), 1.26 (t, J=7.6 Hz, 3H), 1.22-1.05 (m, 4H), 0.89 (s, 3H), 0.86 (s, 3H).

ESI MS: m/z 240.4 (M+H).

The following intermediate compounds were synthesized in accordance to the methods described in the above:

| Aminocrotonate | ESI MS (M + H) | General procedure |
|---|---|---|
| (isobutyl aminocrotonate ethyl ester) | 172.18 | Method-1 |
| (isopentyl aminocrotonate ethyl ester) | 186.0 | Method-1 |
| (neopentyl aminocrotonate ethyl ester) | 186.23 | Method-1 |

-continued
| Aminocrotonate | ESI MS (M + H) | General procedure |
|---|---|---|
| 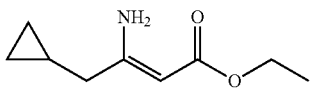 | 170.0 | Method-1 |
| 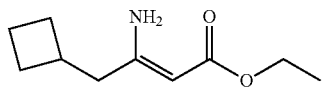 | 184.25 | Method-1 |
| 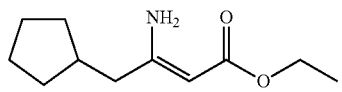 | 198.24 | Method-1 |
| 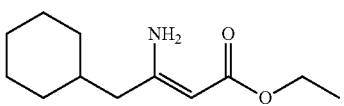 | 212.30 | Method-1 |
| 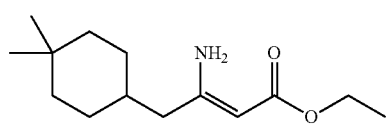 [SMILES: CCOC(=O)/C=C(\N)CC1CCC(C)(C)CC1] | 240.23 | Method-1 |
| 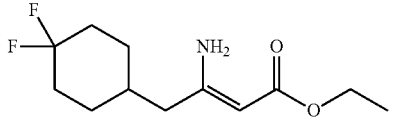 [SMILES: CCOC(=O)/C=C(\N)CC1CCC(F)(F)CC1] | 248.10 | Method-1 |
| 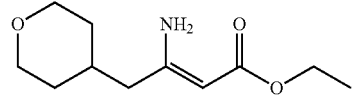 | 214.28 | Method-1 |
| 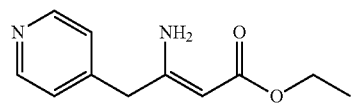 | 207.0 | Method-1 |
| 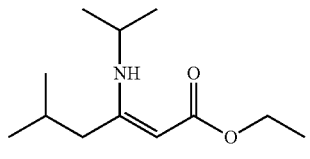 | 214.1 | Method-1 |
| 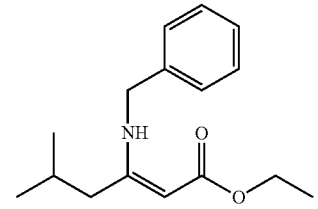 [SMILES: CCOC(=O)/C=C(/CC(C)C)NCc1ccccc1] | 262.0 | Method-1 |

The following 2-aryl malonates were prepared according to the Method-2 using corresponding commercially available malonates and aryl/heterocyclic iodides (see Scheme 2).

| 2-Aryl Malonates | ESI MS (M + H) |
|---|---|
| 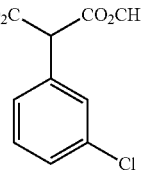 | 243.0 |
|  | 273.0 |
|  | 255.0 |

Example 1

Preparation of 6-((4,4-Dimethylcyclohexyl)methyl)-4-hydroxy-3-phenylpyridin-2(1H)-one Step 1: preparation of Ethyl 2-((4,4-dimethylcyclohexyl)methyl)-4-hydroxy-6-oxo-5-phenyl-1,6-dihydropyridine-3-carboxylate

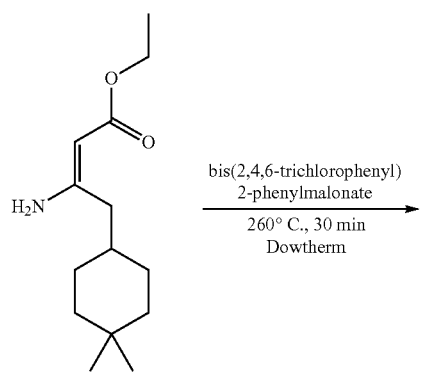

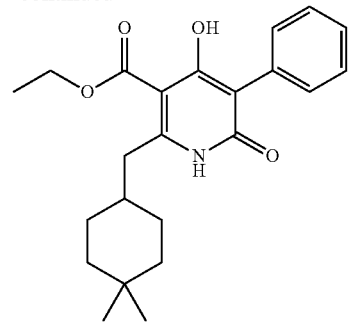

A mixture of ethyl 3-amino-4-(4,4-dimethylcyclohexyl) but-2-enoate (10 g, 41.8 mmol) and bis(2,4,6-trichlorophenyl)-2-phenylmalonate (22.51 g, 41.8 mmol) taken in Dowtherm (45 mL) was heated at 260° C. in a pre-heated sand bath for 30 minutes. The residue obtained was triturated in pet ether and the solid precipitated was filtered, washed with pet ether and dried to afford 7.3 g (46%) of ethyl 2-((4,4-dimethylcyclohexyl)methyl)-4-hydroxy-6-oxo-5-phenyl-1,6-dihydropyridine-3-carboxylate as an off-white solid.

$^1$H NMR (400 MHz, DMSO-d$_6$): δ 11.85-11.75 (br s, 2H), 7.42-7.30 (m, 5H), 4.35 (q, J=6.8 Hz, 2H), 2.83 (d, J=7.2 Hz, 2H), 1.70-1.50 (m, 1H), 1.50-1.05 (m, 11H), 0.88 (s, 6H). ESI MS: m/z 384.21 (M+H).

Step 2: preparation of 6-((4,4-Dimethylcyclohexyl) methyl)-4-hydroxy-3-phenylpyridin-2(1H)-one

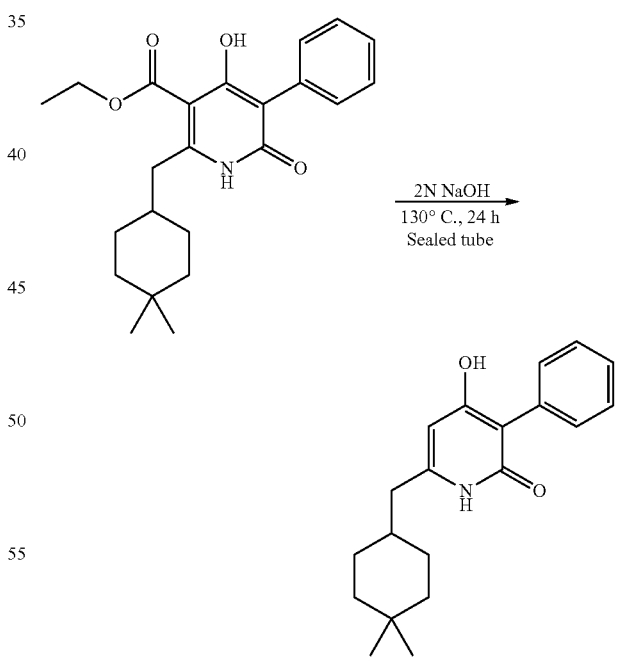

To a solution ethyl 2-((4,4-dimethylcyclohexyl)methyl)-4-hydroxy-6-oxo-5-phenyl-1,6-dihydropyridine-3-carboxylate (55 g, 143.4 mmol) in a sealed tube was added 2N aq NaOH (550 mL) and heated to 130° C. for 24 h. The reaction mixture was diluted with cold water and acidified to pH 2 using aq. 2N HCl solution and the product was extracted into 10% MeOH in CHCl$_3$. The combined organic layer was washed with brine (3×150 mL), dried over anhydrous Na$_2$SO$_4$ and concentrated under vacuum. The crude compound was purified by triturating with n-pentane and diethyl ether as eluent to afford 39 g (87%) of 6-((4,4-dimethylcyclohexyl)methyl)-4-hydroxy-3-phenylpyridin-2(1H)-one as an off-white solid.

$^1$H NMR (400 MHz, DMSO-d$_6$): δ 11.08 (s, 1H), 10.20 (s, 1H), 7.38-7.26 (m, 4H), 7.18-7.14 (m, 1H), 5.78 (s, 1H), 2.30 (d, J=6.1 Hz, 2H), 1.46-1.34 (m, 5H), 1.25 (br s, 4H) 0.87 (d, J=5.3 Hz, 6H). $^{13}$C NMR (100 MHz, DMSO-d$_6$): δ 163.46, 162.82, 146.87, 134.18, 130.77, 126.93, 125.58, 108.39, 98.20, 38.33, 36.76, 32.38, 29.68, 27.99, 24.38.

ESI MS: m/z 312.4 [M+H]. HRMS calcd for C$_{20}$H$_{26}$NO$_2$ [M+H], 312.1958. found, 312.1956. HPLC purity: >99%.

The following compounds were prepared by similar procedures in accordance to the above-described method:

3-(2-Fluorophenyl)-4-hydroxy-6-isobutylpyridin-2(1H)-one

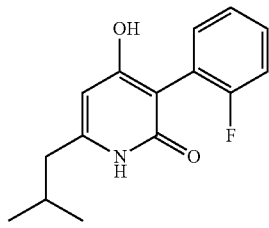 [SMILES: CC(C)Cc1cc(O)c(-c2ccccc2F)c(=O)[nH]1]

$^1$H NMR (400 MHz, DMSO-d$_6$): δ 11.10 (s, 1H), 10.30 (br s, 1H), 7.30-7.22 (m, 2H), 7.14-7.09 (m, 2H), 5.78 (s, 1H), 2.27 (d, J=7.5 Hz, 2H), 1.96-1.89 (m, 1H), 0.90 (d, J=6.6 Hz, 6H).

ESI MS: m/z 262.20 (M+H). HPLC purity: 97.30%.

4-Hydroxy-6-isobutyl-3-phenylpyridin-2(1H)-one

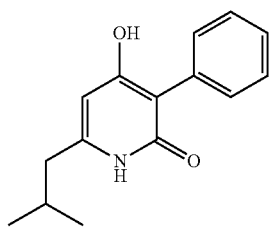 [SMILES: CC(C)Cc1cc(O)c(-c2ccccc2)c(=O)[nH]1]

$^1$H NMR (400 MHz, DMSO-d$_6$): δ 11.18 (br s, 1H), 10.2 (s, 1H), 7.39-7.26 (m, 4H), 7.18-7.15 (m, 1H), 5.80 (s, 1H), 2.30 (d, J=7.10 Hz, 2H), 1.95-1.93 (m, 1H), 0.90-0.88 (d, J=6.42 Hz, 6H).

ESI MS: m/z 244.37 (M+H). HPLC purity: 99.95%.

6-(Cyclopentylmethyl)-4-hydroxy-3-phenylpyridin-2(1H)-one

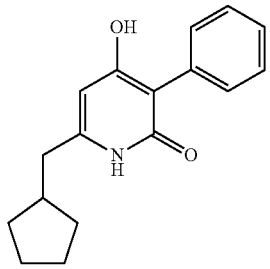 [SMILES: O=c1[nH]c(CC2CCCC2)cc(O)c1-c1ccccc1]

$^1$H NMR (400 MHz, DMSO-d$_6$): δ 11.10 (s, 1H), 10.18 (br s, 1H), 7.38 (d, J=7.50 Hz, 2H), 7.27 (t, J=7.50 Hz, 2H), 7.17 (t, J=7.0 Hz, 1H), 5.86 (s, 1H), 2.40 (s, 2H), 2.16-2.10 (m, 1H), 1.70-1.50 (m, 6H), 1.23-1.19 (m, 2H).

ESI MS: m/z 270.1 (M+H). HPLC purity: 95.96%.

6-((4,4-Difluorocyclohexyl)methyl)-4-hydroxy-3-phenylpyridin-2(1H)-one

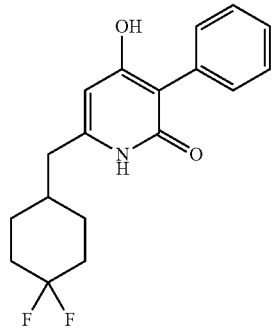 [SMILES: O=c1[nH]c(CC2CCC(F)(F)CC2)cc(O)c1-c1ccccc1]

$^1$H NMR (400 MHz, DMSO-d$_6$): δ 11.08 (s, 1H), 10.18 (s, 1H), 7.37 (m, 2H), 7.28 (m, 2H), 7.17 (m, 1H), 5.80 (s, 1H), 2.36 (d, J=6.6 Hz, 2H), 2.10-1.80 (br. s., 2H), 1.85-1.65 (m, 5H), 1.22 (m, 2H).

ESI MS: m/z 320.2 (M+H). HPLC purity: 99.68%.

Example 2

The following compounds of formula (I) were prepared according to the Method-3A using corresponding 2-substituted malonates and 4-substituted ethyl 3-aminobut-2-enoate prepared using the Method-1 or commercially available sources (see Scheme 3).

43

3-(3-chlorophenyl)-4-hydroxy-6-isobutylpyridin-2(1H)-one

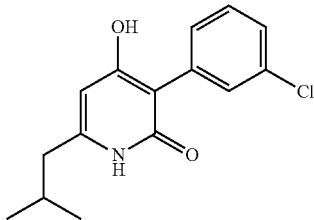 [SMILES: CC(C)Cc1cc(O)c(-c2cccc(Cl)c2)c(=O)[nH]1]

$^1$H NMR (400 MHz, DMSO-d$_6$): δ 11.13 (br s, 1H), 10.59-10.36 (m, 1H), 7.47 (t, J=1.76 Hz, 1H), 7.43-7.38 (m, 1H), 7.31 (t, J=7.91 Hz, 1H), 7.24-7.19 (m, 1H), 5.79 (s, 1H), 2.26 (d, J=7.28 Hz, 2H), 1.98-1.86 (m, 1H), 0.89 (d, J=6.78 Hz, 6H). ESI MS: m/z 278 [M+H]. HPLC purity: 99.0%.

3-(2-chlorophenyl)-4-hydroxy-6-isobutylpyridin-2(1H)-one

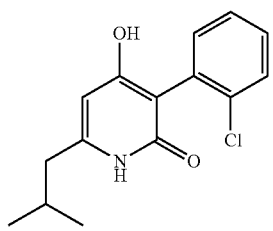 [SMILES: CC(C)Cc1cc(O)c(-c2ccccc2Cl)c(=O)[nH]1]

$^1$H NMR (400 MHz, DMSO-d$_6$): δ 11.06 (br s, 1H), 10.25 (br s, 1H), 7.46-7.39 (m, 1H), 7.31-7.24 (m, 2H), 7.22-7.18 (m, 1H), 5.76 (s, 1H), 2.27 (d, J=7.53 Hz, 2H), 1.98-1.84 (m, 1H), 0.90 (d, J=6.50 Hz, 6H). ESI MS: m/z 278 [M+H]. HPLC purity: 96.4%.

3-(4-fluorophenyl)-4-hydroxy-6-isobutylpyridin-2(1H)-one

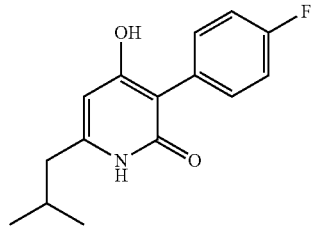 [SMILES: CC(C)Cc1cc(O)c(-c2ccc(F)cc2)c(=O)[nH]1]

$^1$H NMR (400 MHz, DMSO-d$_6$): δ 11.08 (br s, 1H), 10.32 (br s, 1H), 7.49-7.38 (m, 2H), 7.17-7.04 (m, 2H), 5.78 (s, 1H), 2.25 (d, J=7.28 Hz, 2H), 1.98-1.86 (m, 1H), 0.89 (d, J=6.53 Hz, 6H). ESI MS: m/z 262 [M+H]. HPLC purity: 99.2%.

44

3-(3-fluorophenyl)-4-hydroxy-6-isobutylpyridin-2(1H)-one

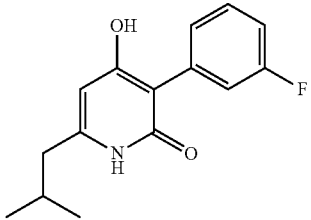 [SMILES: CC(C)Cc1cc(O)c(-c2cccc(F)c2)c(=O)[nH]1]

$^1$H NMR (400 MHz, DMSO-d$_6$): δ 11.10 (br s, 1H), 7.33-7.28 (m, 2H), 7.24 (d, J=8.53 Hz, 1H), 7.02-6.94 (m, 1H), 5.79 (s, 1H), 2.26 (d, J=7.53 Hz, 2H), 1.92 (td, J=6.93, 13.49 Hz, 1H), 0.89 (d, J=6.53 Hz, 6H). ESI MS: m/z 262 [M+H]. HPLC purity: 99.6%.

4-hydroxy-6-isobutyl-3-(2,4,6-trifluorophenyl)pyridin-2(1H)-one

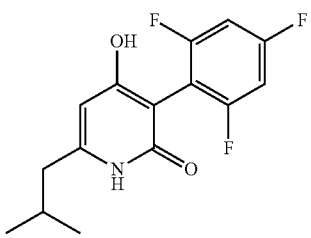 [SMILES: CC(C)Cc1cc(O)c(-c2c(F)cc(F)cc2F)c(=O)[nH]1]

$^1$H NMR (400 MHz, DMSO-d$_6$): δ 11.18 (br s, 1H), 10.68 (br s, 1H), 7.13-7.09 (m, 2H), 5.77 (s, 1H), 2.28 (d, J=7.60 Hz, 2H), 1.96-1.89 (m, 1H), 0.89 (d, J=6.40 Hz, 6H). ESI MS: m/z 298 [M+H]. HPLC purity: 99.4%.

4-hydroxy-6-isopropyl-3-phenylpyridin-2(1H)-one

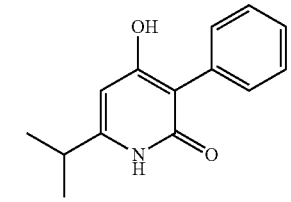 [SMILES: CC(C)c1cc(O)c(-c2ccccc2)c(=O)[nH]1]

$^1$H NMR (400 MHz, DMSO-d$_6$): δ 11.05 (br s, 1H), 10.17 (br s, 1H), 7.37 (d, J=6.80 Hz, 2H), 7.28 (t, J=7.20 Hz, 2H), 7.16 (t, J=7.20 Hz, 1H), 5.82 (s, 1H), 2.71-2.66 (m, 1H), 1.17 (d, J=7.20 Hz, 6H). ESI MS: m/z 230 [M+H]. HPLC purity: 98.4%.

4-hydroxy-6-isopentyl-3-phenylpyridin-2(1H)-one

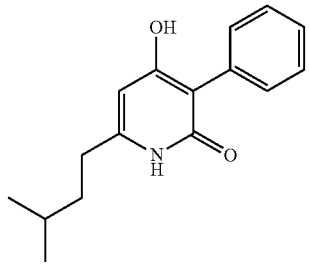 [SMILES: CC(C)CCc1cc(O)c(-c2ccccc2)c(=O)[nH]1]

$^1$H NMR (400 MHz, DMSO-d$_6$): δ 11.09 (br s, 1H), 10.16 (br s, 1H), 7.38 (d, J=7.03 Hz, 2H), 7.28 (t, J=7.53 Hz, 2H), 7.16 (t, J=8.00 Hz, 1H), 5.81 (s, 1H), 2.39 (t, J=8.00 Hz, 2H), 1.55 (td, J=6.56, 13.24 Hz, 1H), 1.50-1.41 (m, 2H), 0.90 (d, J=6.53 Hz, 6H). ESI MS: m/z 258 [M+H]. HPLC purity: 99.0%.

4-hydroxy-6-neopentyl-3-phenylpyridin-2(1H)-one

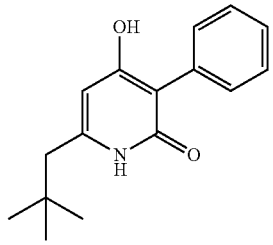 [SMILES: CC(C)(C)Cc1cc(O)c(-c2ccccc2)c(=O)[nH]1]

$^1$H NMR (400 MHz, DMSO-d$_6$): δ 10.92 (br s, 1H), 10.22 (br s, 1H), 7.40 (d, J=6.80 Hz, 2H), 7.28 (t, J=7.60 Hz, 2H), 7.16 (t, J=7.20 Hz, 1H), 5.77 (s, 1H), 2.31 (s, 2H), 0.94 (s, 9H). ESI MS: m/z 258 [M+H]. HPLC purity: 95.7%.

6-(cyclopropylmethyl)-4-hydroxy-3-phenylpyridin-2(1H)-one

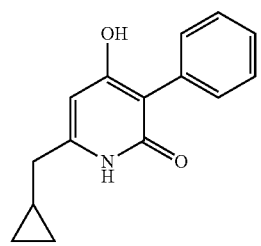 [SMILES: O=c1[nH]c(CC2CC2)cc(O)c1-c1ccccc1]

$^1$H NMR (400 MHz, DMSO-d$_6$): δ 11.08 (br s, 1H), 7.42-7.35 (m, 2H), 7.32-7.23 (m, 2H), 7.20-7.13 (m, 1H), 5.94 (s, 1H), 2.30 (d, J=7.03 Hz, 2H), 1.06-0.94 (m, 1H), 0.55-0.45 (m, 2H), 0.25-0.18 (m, 2H). ESI MS: m/z 242 [M+H]. HPLC purity: 99.3%.

6-(cyclobutylmethyl)-4-hydroxy-3-phenylpyridin-2(1H)-one

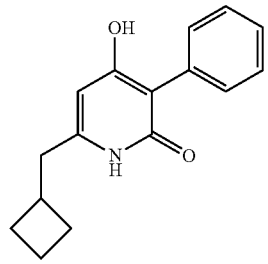

$^1$H NMR (400 MHz, DMSO-d$_6$): δ 11.04 (br s, 1H), 10.16 (br s, 1H), 7.40-7.35 (m, 2H), 7.27 (t, J=7.65 Hz, 2H), 7.19-7.13 (m, 1H), 5.77 (s, 1H), 2.62-2.52 (m, 1H), 2.08-1.99 (m, 2H), 1.88-1.79 (m, 2H), 1.74-1.63 (m, 2H). ESI MS: m/z 256 [M+H]. HPLC purity: 99.8%.

6-(cyclohexylmethyl)-4-hydroxy-3-phenylpyridin-2(1H)-one

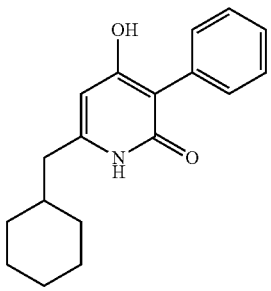 [SMILES: O=c1[nH]c(CC2CCCCC2)cc(O)c1-c1ccccc1]

$^1$H NMR (400 MHz, DMSO-d$_6$): δ 11.00 (br s, 1H), 10.19 (s, 1H), 7.39 (d, J=7.03 Hz, 2H), 7.27 (t, J=7.53 Hz, 2H), 7.19-7.12 (m, 1H), 5.76 (s, 1H), 2.26 (d, J=6.78 Hz, 2H), 1.73-1.52 (m, 6H), 1.27-1.09 (m, 3H), 0.85-0.99 (m, 2H). $^{13}$C NMR (100 MHz, DMSO-d$_6$): δ 163.45, 162.73, 146.75, 134.13, 130.76, 126.92, 125.59, 108.39, 98.17, 36.82, 32.24, 25.82, 25.52. HPLC purity: >99%. ESI MS: m/z 284 [M+H]. HRMS calcd for C$_{18}$H$_{22}$NO$_2$ [M+H]$^+$, 284.1645; found, 284.1647.

6-benzyl-4-hydroxy-3-phenylpyridin-2(1H)-one

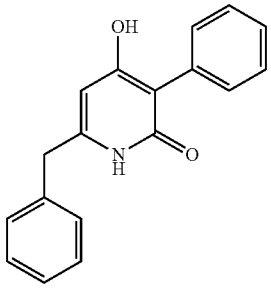 [SMILES: O=c1[nH]c(Cc2ccccc2)cc(O)c1-c1ccccc1]

$^1$H NMR (400 MHz, DMSO-d$_6$): δ 11.27 (br s, 1H), 10.18 (br s, 1H), 7.40-7.31 (m, 6H), 7.27 (t, J=7.65 Hz, 3H), 7.19-7.13 (m, 1H), 5.70 (s, 1H), 3.75 (s, 2H). ESI MS: m/z 278 [M+H]. HPLC purity: 98.9%.

4-hydroxy-3-phenyl-6-((tetrahydro-2H-pyran-4-yl)methyl)pyridin-2(1H)-one

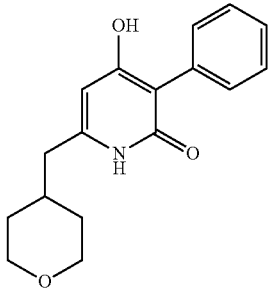 [SMILES: O=c1[nH]c(CC2CCOCC2)cc(O)c1-c1ccccc1]

$^1$H NMR (400 MHz, DMSO-d$_6$): δ 11.08 (br s, 1H), 10.18 (br s, 1H), 7.40-7.35 (m, 2H), 7.31-7.24 (m, 2H), 7.20-7.13 (m, 1H), 5.80 (s, 1H), 3.83 (dd, J=3.01, 11.54 Hz, 2H), 3.30-3.22 (m, 2H), 2.33 (d, J=7.28 Hz, 2H), 1.82 (br. s., 1H), 1.52 (d, J=12.30 Hz, 2H), 1.28-1.15 (m, 2H). ESI MS: m/z 286 [M+H]. HPLC purity: 98.5%.

Example 3

The following compound of formula (I) was prepared according to the Method-3B and Method-4B using corresponding 2-aryl malonates and 4-substituted ethyl 3-aminobut-2-enoate made using the Method-1 or commercially available sources (Scheme 4 and Scheme 6).

4-Hydroxy-3-phenyl-6-(pyridin-4-ylmethyl)pyridin-2(1H)-one

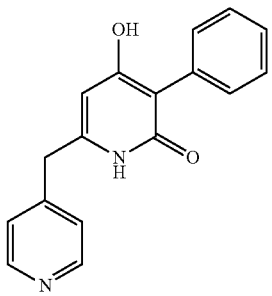 [SMILES: O=c1[nH]c(Cc2ccncc2)cc(O)c1-c1ccccc1]

$^1$H NMR (400 MHz, DMSO-d$_6$): δ 11.39 (s, 1H), 10.3 (br s, 1H), 8.54 (d, J=4.8 Hz, 2H), 7.36-7.26 (m, 6H), 7.18 (m, 1H), 5.75 (s, 1H), 3.8 (s, 2H). ESI MS: m/z 279.1 (M+H). HPLC purity: 94.77%.

Example 4

The following compound of formula (I) was prepared according to the Method-3C using corresponding 2-aryl malonates and 4-substituted ethyl 3-aminobut-2-enoate prepared using the Method-1 or commercially available sources (Scheme 5). Cyclisation and decarboxylation was observed in one step without base and acid.

3-(2,4-Difluorophenyl)-4-hydroxy-6-isobutylpyridin-2(1H)-one (NV-035-PD-54-C)

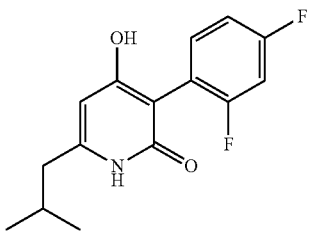

$^1$H NMR (400 MHz, DMSO-d$_6$): δ 11.10 (s, 1H), 10.60 (br s, 1H), 7.29-7.25 (m, 1H), 7.16-6.99 (m, 2H), 5.77 (s, 1H), 2.26 (d, J=7.0 Hz, 2H), 1.90-1.94 (m, 1H), 0.89 (d, J=6.1 Hz, 6H). ESI MS: m/z 280.23 (M+H)$^+$. HPLC purity: 99.03%.

Example 5

Preparation of 4-hydroxy-6-isobutyl-1-methyl-3-phenylpyridin-2(1H)-one

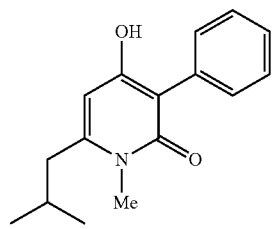

Step-1: preparation of 6-isobutyl-2-oxo-3-phenyl-1,2-dihydropyridin-4-yl acetate

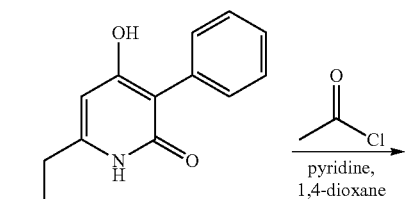

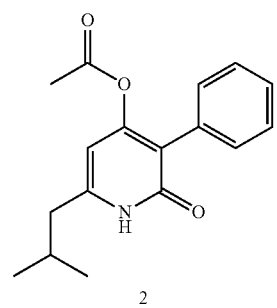

To a suspension of pyridone 1 (50.8 mg, 0.209 mmol) in 1,4-dioxane (3 mL) and cooled to 0° C. was added acetyl chloride (16 uL, 0.219 mmol) and pyridine (18.5 uL, 0.230 mmol). The mixture was allowed to gradually warm to rt and stirred at rt for 2 hr. The reaction mixture was concentrated in vacuo and the residue was taken up in DCM (3 mL). The organic layer was washed with water, brine, dried over $Na_2SO_4$ and concentrated in vacuo to give light yellow residue. The residue was purified by column chromatography (ISCO Combiflash®, 4 g silica gel column, 0-40% EtOAc/cyclohexanes) to give compound 2 as white solid (37.6 mg, 63% yield).

$^1$H NMR (400 MHz, $CDCl_3$): δ 7.47-7.33 (m, 5H), 6.21 (s, 1H), 2.50 (d, J=7.28 Hz, 2H), 2.15-2.09 (m, 1H), 2.07 (s, 3H), 1.00 (d, J=6.53 Hz, 6H). ESI MS: m/z 286 [M+H].

Step-2: preparation of 6-isobutyl-1-methyl-2-oxo-3-phenyl-1,2-dihydropyridin-4-yl acetate (3) and 6-isobutyl-2-methoxy-3-phenylpyridin-4-yl acetate (4)

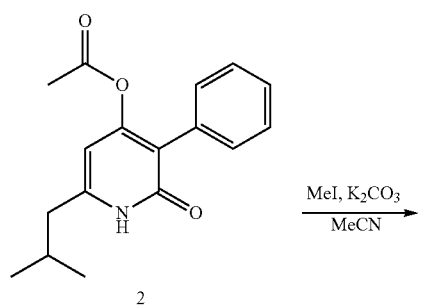

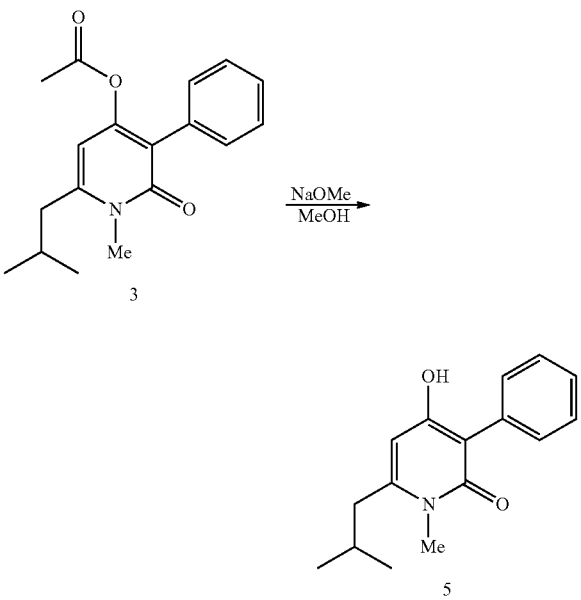

To a solution of pyridone 2 (37.6 mg, 0.132 mmol) in dry MeCN (2 mL) was added $K_2CO_3$ (18.2 mg, 0.132 mmol) and MeI (11 uL, 0.172 mmol). The resultant mixture was heated at 100° C. for 30 minutes in Biotage microwave reactor. Reaction mixture was cooled and diluted with EtOAc (4 mL). The organics were washed sequentially with water and brine, dried over $Na_2SO_4$, filtered and concentrated in vacuo to give colorless oil. The crude material was purified by column chromatography (ISCO Combiflash®, 4 g silica gel column, 0-50% EtOAc/cyclohexanes) to give compound 3 (26 mg, 65% yield).

6-isobutyl-1-methyl-2-oxo-3-phenyl-1,2-dihydropyridin-4-yl acetate (3): $^1$H NMR (400 MHz, $CDCl_3$): δ 7.16-7.32 (m, 5H), 5.83 (s, 1H), 3.45 (s, 3H), 2.42 (d, J=7.20 Hz, 2H), 1.91 (s, 3H), 1.83-1.88 (m, 1H), 0.94 (d, J=6.40 Hz, 6H). ESI MS: [M-Ac] m/z 258.

Step-3: Preparation of 4-hydroxy-6-isobutyl-1-methyl-3-phenylpyridin-2(1H)-one (5)

To a solution of 3 (26 mg, 0.087 mmol) in MeOH (2 mL) was added 30% NaOMe in MeOH (0.2 mL, 10% v/v) at RT. The resultant mixture was stirred at rt for 30 minutes before it was concentrated under vacuo to give a white residue. The white residue was taken up in EtOAc (3 mL) and washed with 10% citric acid solution, dried over $Na_2SO_4$, filtered and concentrated in vacuo to give a white residue. The crude material was dissolved in MeOH and purified on reversed-phase HPLC using solvent gradient of 20-95% MeCN/0.1% formic acid in $H_2O$ to give desired product 5 as a white solid (10.3 mg, 46% yield).

$^1$H NMR (400 MHz, DMSO-$d_6$): δ 7.35 (d, J=7.20 Hz, 2H), 7.28 (t, J=7.60 Hz, 2H), 7.17 (t, J=7.20 Hz, 1H), 5.89 (s, 1H), 3.36 (s, 3H), 2.47 (s, 2H), 1.94-1.87 (m, 1H), 0.97 (d, J=6.80 Hz, 6H)). ESI MS: m/z 258 [M+H]. HPLC purity: >99%.

Example 6

Preparation of 4-Hydroxy-2-isobutyl-6-oxo-5-phenyl-1,6-dihydropyridine-3-carboxamide

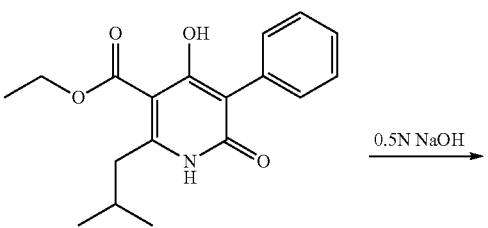

-continued

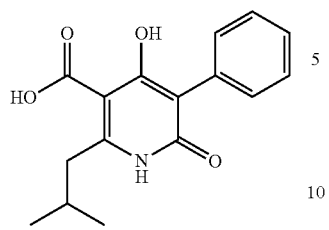

A suspension of 200 mg of ethyl 4-hydroxy-2-isobutyl-6-oxo-5-phenyl-1,6-dihydropyridine-3-carboxylate in 0.5N NaOH was heated at reflux temperature. After 4 h the reaction mass diluted with ice water and acidified with 1N HCl, resultant solid was filtered. The solid mass was dissolved in ethyl acetate and extracted with saturated NaHCO$_3$ solution (4×30 mL). The combined bicarbonate solution was acidified with con. HCl and the resultant solid was filtered, washed with water and dried to afford 20 mg of 4-hydroxy-2-isobutyl-6-oxo-5-phenyl-1,6-dihydropyridine-3-carboxylic acid 3 as an off white solid.

$^1$H NMR (400 MHz, DMSO-d$_6$): δ 13.6-13.2 (br s, 1H), 11.78 (s, 1H), 7.42-7.3 (m, 4H), 7.27-7.2 (m, 1H), 2.91 (d, J=6.6 Hz, 2H), 1.61 (br s, 1H), 1.42-1.05 (m, 8H), 0.87 (s, 6H).

ESI MS: m/z 356.4 (M+H). HPLC purity: 92.3%.

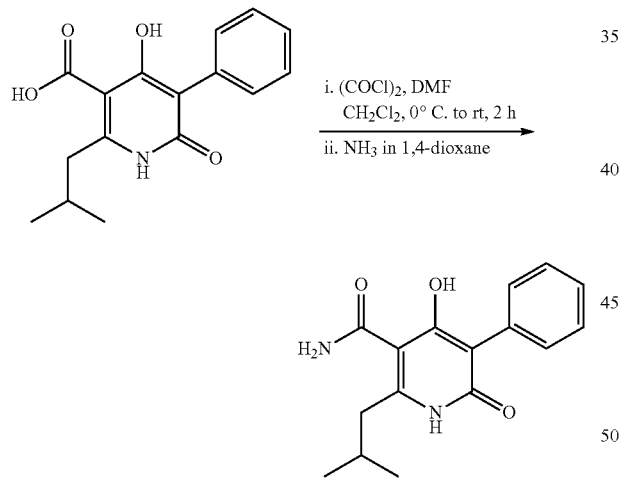

To a cold solution of 4-hydroxy-2-isobutyl-6-oxo-5-phenyl-1,6-dihydropyridine-3-carboxylic acid 3 (400 mg, 13.94 mmol), DMF (4 drops) in DCM (20 mL) was added oxalyl chloride (1.2 mL, 139.4 mmol) at 0° C. slowly and stirred at rt for 2 h. The reaction mass quenched with NH$_3$ in 1,4-dioxane and stirred for 10 min, concentrated. The crude product was purified by prep. HPLC to afford 28 mg (7%) of 4-hydroxy-2-isobutyl-6-oxo-5-phenyl-1,6-dihydropyridine-3-carboxamide as off white solid.

$^1$H NMR (400 MHz, DMSO-d$_6$): δ 10.85 (br s, 1H), 8.17 (s, 1H), 7.43-7.34 (m, 2H), 7.28-7.13 (m, 3H), 2.7 (d, J=6.7 Hz, 2H), 1.99-1.90 (m, 1H), 0.86 (d, J=6.4 Hz, 6H). ESI MS: m/z 287.19 (M+H). HPLC purity: 94.32%.

Example 7

Preparation of ((6-((4,4-dimethylcyclohexyl)methyl)-2-oxo-3-phenyl-1,2-dihydropyridin-4-yl)oxy)methyl dihydrogen phosphate

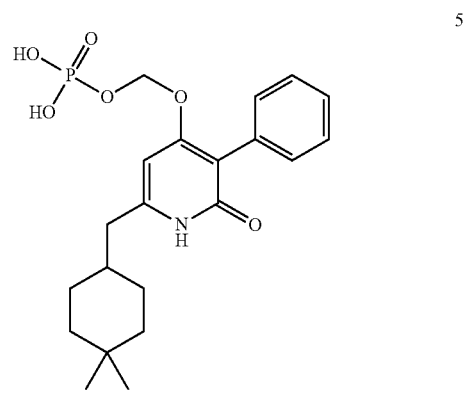 [SMILES: CC1(C)CCC(Cc2cc(OCOP(=O)(O)O)c(-c3ccccc3)c(=O)[nH]2)CC1]

Step-1: Preparation of Dibenzyl (6-((4,4-dimethylcyclohexyl)methyl)-2-oxo-3-phenyl-1,2-dihydropyridin-4-yloxy)methyl phosphate 9

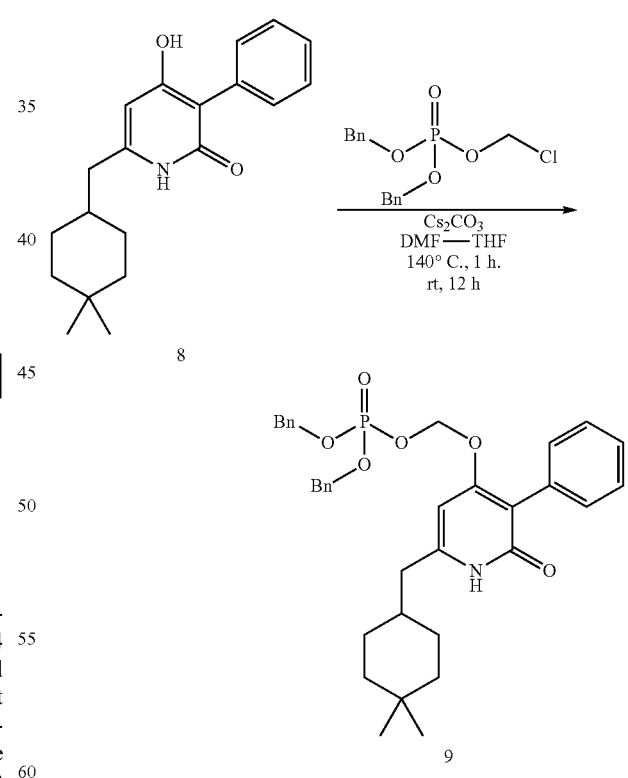

A mixture of 6-((4,4-dimethylcyclohexyl)methyl)-4-hydroxy-3-phenylpyridin-2(1H)-one 8 (4 g, 12.84 mmol) and Cs$_2$CO$_3$ (4.59 g, 14.12 mmol) in DMF (20 mL) and THF (20 mL) was heated at 140° C. for 1 h. The reaction mixture was cooled to rt and added a solution of dibenzyl chloromethyl phosphate (4.88 g, 14.97 mmol) in DMF-THF (1:1, 4 mL)

slowly drop-wise. The reaction mixture was stirred at rt for 12 h. All the reaction mixture was diluted with cold water and extracted with EtOAc (3×50 mL). The combined organic layer washed with water (3×50 mL), brine, dried over Na$_2$SO$_4$ and concentrated to afford 7.5 g of crude dibenzyl (6-((4,4-dimethylcyclohexyl)methyl)-2-oxo-3-phenyl-1,2-dihydropyridin-4-yloxy)methyl phosphate 9. The crude product was taken to the next step without further purification.

9: ESI MS: m/z 602.21 [M+H]$^+$ & 603.23 [M+H]$^+$

Step-2: Preparation of (6-((4,4-Dimethylcyclohexyl)methyl)-2-oxo-3-phenyl-1,2-dihydropyridin-4-yloxy)methyl dihydrogen phosphate To a solution of dibenzyl (6-((4,4-dimethylcyclohexyl)methyl)-2-oxo-3-phenyl-1,2-dihydropyridin-4-yloxy)methyl phosphate 9 (7.5 g, crude) in EtOH (150 mL) was added 10% Pd/C (2.2 g). The resulting mixture was stirred under Hydrogen balloon pressure for 1 h. The reaction mixtures was filtered through a Celite bed and washed with MeOH. The filtrate was concentrated under reduced pressure to get 5 g of crude material. This crude material was purified on reversed-phase HPLC using X-bridge column (C-18, 150×30 mm ID5) using solvent gradient of 0-95% MeCN/0.05% TFA in H$_2$O to give the title compound as a white solid (840 mg, 15.5% for two steps).

((6-((4,4-dimethylcyclohexyl)methyl)-2-oxo-3-phenyl-1,2-dihydropyridin-4-yl)oxy)methyl dihydrogen phosphate:

$^1$H NMR (400 MHz, DMSO-d$_6$): δ 11.7-11.3 (br, 1H), 7.37 (d, J=7.2 Hz, 2H), 7.30 (dd, J=7.6, 7.2 Hz, 2H), 7.21 (t, J=7.2 Hz, 1H), 6.17 (s, 1H), 5.47 (s, 1H), 5.45 (s, 1H), 2.40 (d, J=6.8 Hz, 2H) 1.60-1.42 (m, 3H), 1.40-1.30 (m, 2H), 1.20-1.10 (m, 4H), 0.90 (s, 3H), 0.87 (s, 3H). $^{13}$C NMR (100 MHz, DMSO-d$_6$): δ 163.1 (1C), 161.7 (1C), 148.5 (1C), 133.1 (1C), 130.9 (2C), 127.25 (2C), 126.3 (1C), 111.9 (1C), 95.4 (1C), 86.8 (1C), 38.4 (1C), 37.1 (1C), 32.5 (1C), 29.8 (2C), 28.1 (2C), 24.4 (1C).

ESI MS: m/z 422.20 [M+H]. HPLC purity: 96.9%.

Example 8

Preparation of 6-((4,4-dimethylcyclohexyl)methyl)-2-oxo-3-phenyl-1,2-dihydropyridin-4-yl dihydrogen phosphate Step-1: preparation of tetrabenzyl (6-((4,4-dimethylcyclohexyl)methyl)-3-phenylpyridine-2,4-diyl) bis(phosphate)

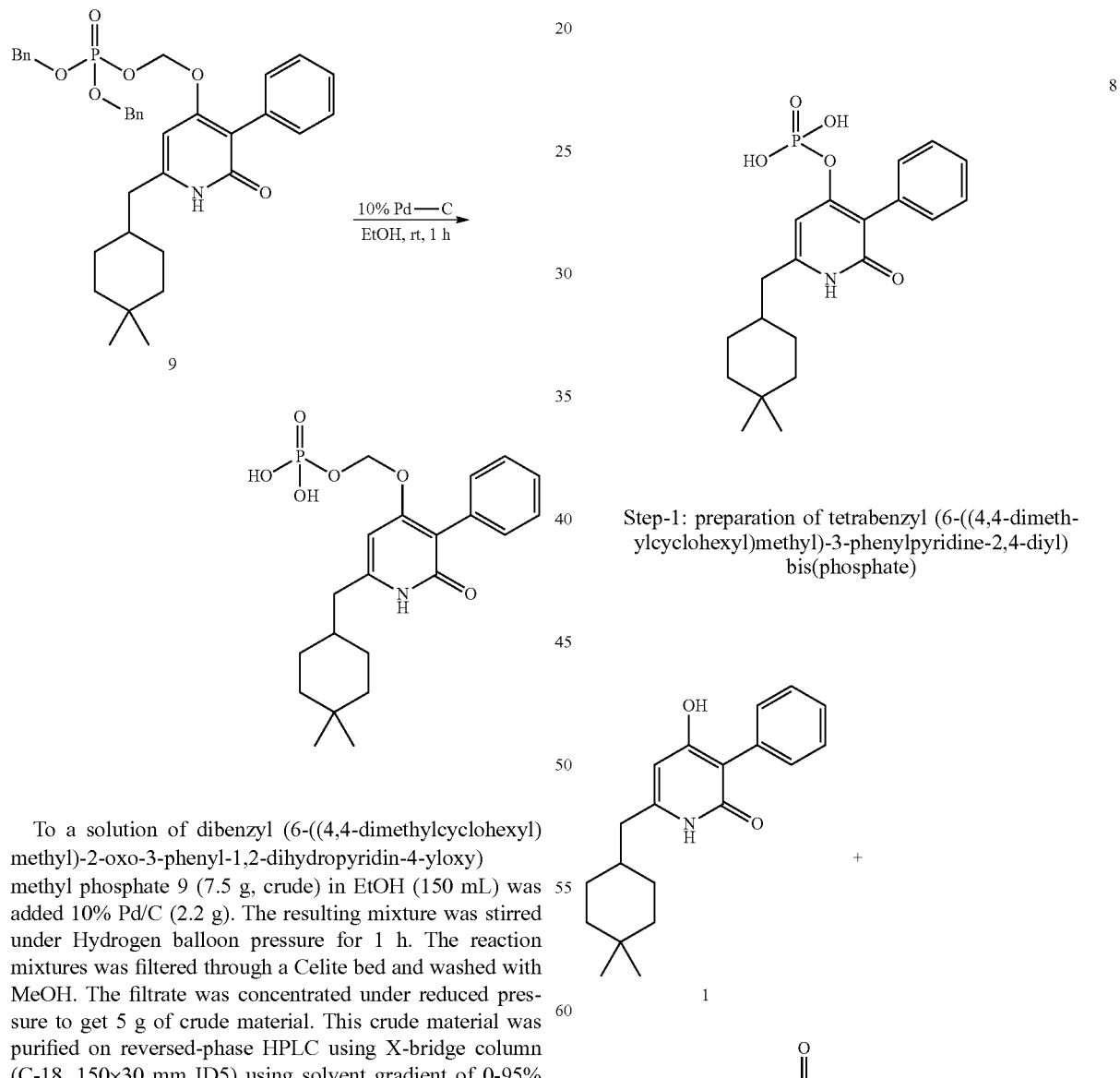

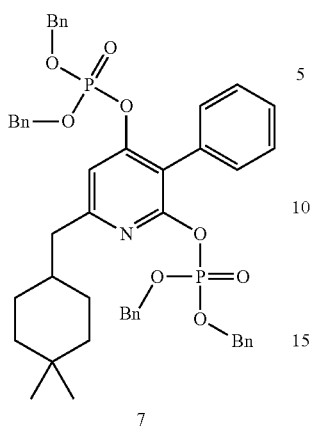

7

To a suspension of pyridone 1 (614.7 mg, 1.974 mmol) in dry DMF (10 mL) and cooled to 0° C. was added $K_2CO_3$ (818 mg, 5.92 mmol) followed by dibenzyl phosphorochloridate (11.7 mL, 3.965 mmol, 10% w/v in benzene). The resultant mixture was allowed to gradually warm up to rt and stirred at rt for 18 hrs. The reaction mixture was diluted with EtOAc (15 mL) and water (10 mL) was added. The organics were separated and the aq layer was extracted with EtOAc (3×8 mL). The combined organics were washed with water and brine, dried over $Na_2SO_4$, filtered and concentrated in vacuo to give yellow oil. Crude material was purified by column chromatography (ISCO Combiflash®, 40 g silica gel column, 0-30% EtOAc/cyclohexanes) to give pyridone 7 as white solid (1.45 g, 89% yield).

$^1$H NMR (400 MHz, $CDCl_3$): δ 7.44-7.28 (m, 17H), 7.25-7.21 (m, 4H), 7.21-7.13 (m, 4H), 7.07 (s, 1H), 5.11-5.02 (m, 4H), 4.87-4.75 (m, 4H), 2.56 (d, J=7.03 Hz, 2H), 1.47 (br s, 2H), 1.43 (s, 1H), 1.34-1.27 (m, 2H), 1.19-1.03 (m, 4H), 0.86 (s, 6H). ESI MS: m/z 832 [M+H]$^+$.

Step-2: Preparation of 6-((4,4-dimethylcyclohexyl)methyl)-2-oxo-3-phenyl-1,2-dihydropyridin-4-yl dihydrogen phosphate

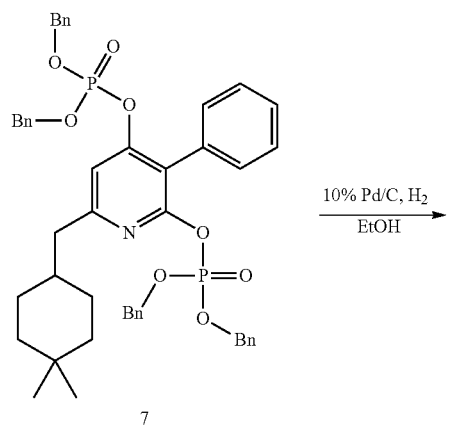

7

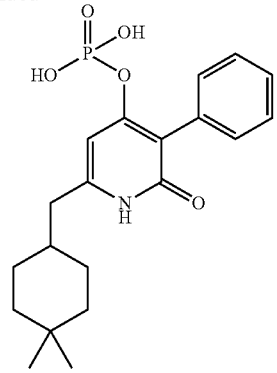

8

A solution of di-phosphorylated material 6 (1.00 g, 1.326 mmol) in 2:1 EtOH/EtOAc (45 mL) was purged with Argon before 10% Pd/C (150 mg, 15% w/w) was added. The resultant mixture was left to stir at rt under hydrogen atmosphere for 3 hrs. The reaction mixture was purged with argon before it was filtered through a plug of celite, washing with MeOH. The filtrate was concentrated in vacuo to give a brown residue. The crude material was dissolved in DMSO and purified on reversed-phase HPLC using solvent gradient of 10-95% MeCN/0.1% formic acid in $H_2O$ to give the title compound as white solid (280.5 mg, 54% yield).

$^1$H NMR (400 MHz, DMSO-$d_6$): δ 11.59 (br s, 1H), 7.41-7.35 (m, 2H), 7.34-7.27 (m, 2H), 7.27-7.20 (m, 1H), 6.36 (s, 1H), 2.37 (d, J=6.78 Hz, 2H), 1.47 (br s, 3H), 1.35 (d, J=8.53 Hz, 2H), 1.21-1.08 (m, 4H), 0.89 (s, 3H), 0.87 (s, 3H). ESI MS: m/z 392 [M+H]$^+$. HPLC purity: 95%. HRMS calcd for $C_{20}H_{25}NO_6P$ [M−H]$^-$, 390.1476; found, 390.1487.

PHARMACOLOGICAL DATA

The utility of the compounds of the present invention may be evidenced by using any one of the assays described herein below.

The following abbreviations used herein below have the corresponding meanings:
Mtb: *Mycobacterium tuberculosis*
TB: Tuberculosis
H37Rv: Laboratory strain of Mtb from ATCC (catalogue #27294)
ATCC: American type culture collection
ADS: Albumin: Dextrose: Sodium chloride
DMSO: Dimethyl sulfoxide
MoA: Mechanism of action
MIC: Minimum inhibitory concentration Bacterial Strain, Culture Media and Chemicals

*Mycobacterium tuberculosis* H37Rv (ATCC #27294) (Mtb) strain was maintained in Middlebrook 7H9 broth medium supplemented with 0.05% Tween 80 and 10% ADS supplement. ADS supplement contains 5% bovine serum albumin fraction V, 2% D-dextrose and 0.8% of sodium chloride. Middlebrook 7H11 agar medium supplemented with 10% OADC (oleic acid, albumin, dextrose and catalase) was used as solid media for growing Mtb. Stock solutions of the compounds were prepared using 90% DMSO.

Minimum Inhibitory Concentration ($MIC_{50}$) Determination

In Table 2 below, $MIC_{50}$ is defined as the lowest concentration of the compound that inhibited 50% growth of the wild type strain compared to untreated controls. Test compounds were two or three fold serially diluted in duplicates and spotted by mosquito HTS to 384-well clear plates, resulting in 10 dilutions of each compound. A volume of 50 µl of Mtb culture (final $OD_{600}$ of 0.02) was added to each well, and the assay plates were incubated at 37° C. for 5 days. Growth of bacteria was measured by reading absorbance at 600 nM using a Spectramax M2 spectrophotometer. $MIC_{50}$ values were determined by using Activity Base software.

TABLE 2

| Compound No. | Compound Structure | MTB $MIC_{50}$ µM |
|---|---|---|
| PD14 | 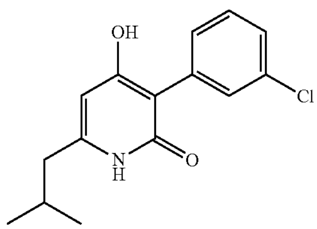 [SMILES: CC(C)Cc1cc(O)c(-c2cccc(Cl)c2)c(=O)[nH]1] | 2.67 |
| PD15 | 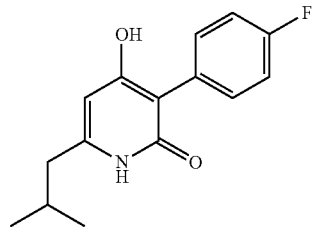 [SMILES: CC(C)Cc1cc(O)c(-c2ccc(F)cc2)c(=O)[nH]1] | 6.75 |
| PD18 | 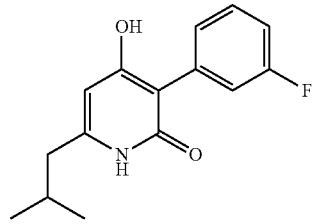 [SMILES: CC(C)Cc1cc(O)c(-c2cccc(F)c2)c(=O)[nH]1] | 2.69 |
| PD17 | 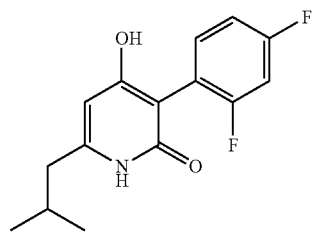 [SMILES: CC(C)Cc1cc(O)c(-c2ccc(F)cc2F)c(=O)[nH]1] | 9.18 |
| PD12 | 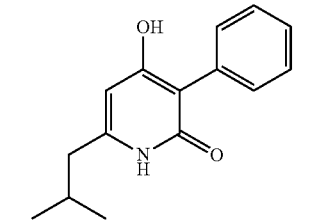 [SMILES: CC(C)Cc1cc(O)c(-c2ccccc2)c(=O)[nH]1] | 1.90 |

TABLE 2-continued

| Compound No. | Compound Structure | MTB $MIC_{50}$ µM |
|---|---|---|
| PD7 | 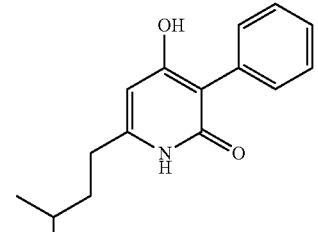 | 1.51 |
| PD8 | 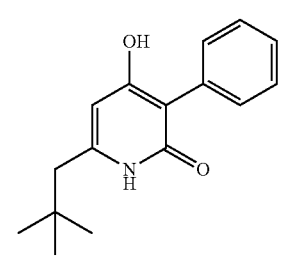 [SMILES: CC(C)(C)Cc1cc(O)c(-c2ccccc2)c(=O)[nH]1] | 10.04 |
| PD3 | 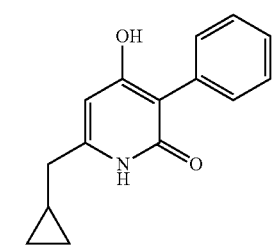 [SMILES: O=c1[nH]c(CC2CC2)cc(O)c1-c1ccccc1] | 4.53 |
| PD5 | 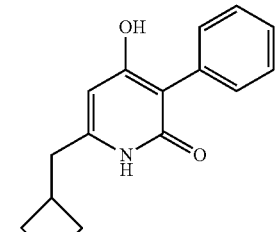 | 1.19 |
| PD4 | 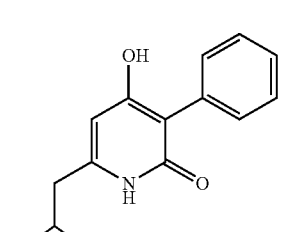 | 0.92 |

TABLE 2-continued
| Compound No. | Compound Structure | MTB MIC$_{50}$ μM |
|---|---|---|
| PD2 | 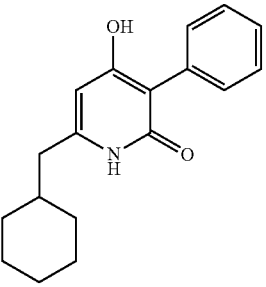 [SMILES: O=c1[nH]c(CC2CCCCC2)cc(O)c1-c1ccccc1] | 0.22 |
| PD10 | 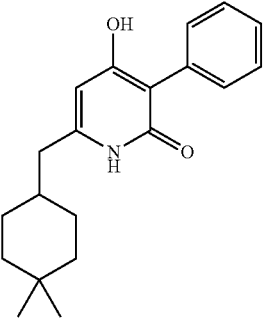 [SMILES: CC1(C)CCC(Cc2cc(O)c(-c3ccccc3)c(=O)[nH]2)CC1] | 0.020 |
| PD9 | 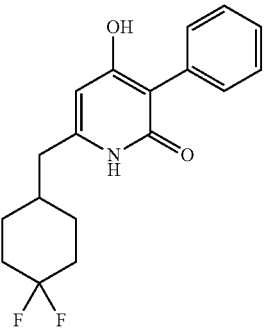 [SMILES: O=c1[nH]c(CC2CCC(F)(F)CC2)cc(O)c1-c1ccccc1] | 1.32 |
| PD1 | 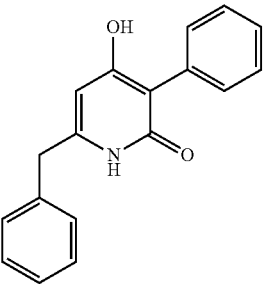 [SMILES: O=c1[nH]c(Cc2ccccc2)cc(O)c1-c1ccccc1] | 1.40 |
| PD11 | 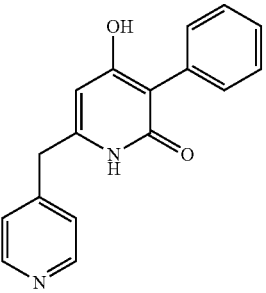 [SMILES: O=c1[nH]c(Cc2ccncc2)cc(O)c1-c1ccccc1] | 6.08 |
| PD6 | 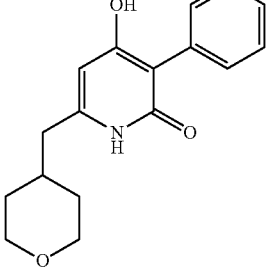 | 10.10 |
| PD19 | 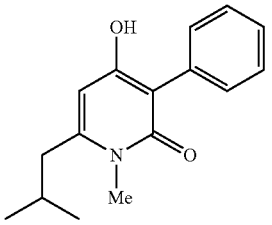 [SMILES: CC(C)Cc1cc(O)c(-c2ccccc2)c(=O)n1C] | 8.14 |
| PD21 | 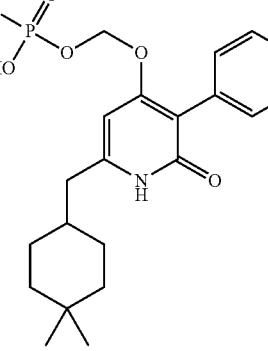 | 3.99 |
| PD22 | 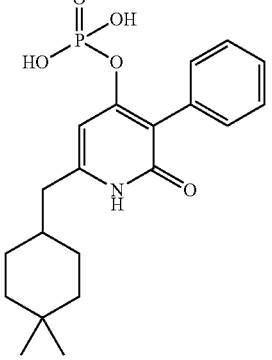 | 1.72 |
| PD13 | 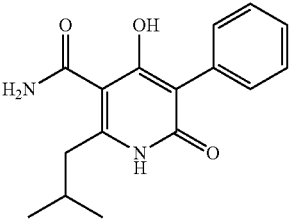 [SMILES: CC(C)Cc1[nH]c(=O)c(-c2ccccc2)c(O)c1C(N)=O] | 18.7 |
Various in vitro and in vivo assays can be used to show utility of the compounds of the present invention, such as bactericidal activity, activity against starvation or hypoxic non-replicating bacteria, activity against macrophage-intracellular bacteria, acute and established animal efficacy studies in diverse species like mouse, rat, guinea-pigs, rabbits, monkey, etc. See, Pethe K, et. al., "A chemical genetic screen in *Mycobacterium tuberculosis* identifies carbon-source-dependent growth inhibitors devoid of in vivo efficacy", *Nat. Commun,* 1(57), 1-8 (2010); and Wayne, L. G. In *Mycobacterium Tuberculosis Protocols*, Parish, T., Stoker, N. G., Eds., Humana Press, Totowa, N.J., pp 247-270 (2001).

Mechanism of Action (MoA):
Mode of Action Studies.

To evaluate the mode of action of the compounds of formula (I), spontaneous resistant mutants of Mtb were generated against selected compounds of formula (I) (e.g., compound Nos. PD12, PD10 and PD2). Briefly, $10^9$ colony forming units of Mtb H37Rv were plated onto 7H11 plates containing 7.5 and 10 μM concentration of PD12, PD10 and PD2. These plates were incubated at 37° C. incubator for 3 weeks. Colonies formed on the plates were further subcultured in the absence of antibiotics and resistance to PD12, PD10 and PD2 were confirmed by MIC determination. Genomic DNA from selected six spontaneous resistant isolates was isolated and subjected to whole genome sequencing using Solexa system as reported in Pethe K, et. al., "A chemical genetic screen in *Mycobacterium tuberculosis* identifies carbon-source-dependent growth inhibitors devoid of in vivo efficacy", *Nat. Commun,* 1(57), 1-8 (2010). Computational analysis and further capillary sequencing results revealed that the mutations in all spontaneous resistant mutants are mapped to Rv1484 gene encoding inhA. Five of the mutants showed single nucleotide polymorphism resulting in one of the following amino acid changes in inhA namely D148G, S94A, G96V and D148V (See Table 3 below).

TABLE 3

| Strains | inhA genotype | Compound MIC$_{50}$ (μM) | | | Isoniazid | Ethionamide |
| --- | --- | --- | --- | --- | --- | --- |
| | | PD12 | PD2 | PD10 | | |
| H37Rv WT | WT inhA | 1.54 | 0.16 | 0.05 | 0.25 | 1.66 |
| 529-5X-108-S1 | gac to ggc D148G | >40 | 1.46 | 0.29 | 0.15 | 1.53 |
| 529-5X-108-B2 | tcg to gcg S94A | >40 | 4.04 | 0.78 | 0.86 | 9.74 |
| 529-5X-108-S3 | gac to ggc D148G | >40 | 1.73 | 0.38 | 0.15 | — |
| 529-5X-108-B4 | ggg to gtg G96V | >40 | 14.60 | >5.0 | 0.09 | 1.32 |
| 529-10X-108-B6 | — | >40 | >40 | >5.0 | 0.11 | 1.41 |
| 529-10X-107-B8 | gac to gaa D148E | >40 | >40 | >5.0 | 0.31 | 1.91 |

Similarly in *M bovis* BCG and *M. smegmatis* PD12 and PD2 spontaneous resistant mutants also mapped mutations in InhA (M161I, M161V and T17A), See Table 4 below, the enoyl-ACP reductase catalyzes the NADH-dependent reduction of long chain trans-2-enoyl ACP fatty acids and is an important component of mycobacterial FAS (fatty acids synthase) II system (Quemard et al 1995). Further, the genetic complementation and lipid profiling $^{14}$C-acetate tracer incorporation studies confirmed the molecular target of the compounds of formula (I) in Mtb is inhA. One of the most effective and extensively used drugs for the treatment of TB is isoniazid (INH). INH is a prodrug that need activation by KatG (mycobacterial catalase peroxidase) enzyme, activated form of INH reacts with NADH+ to form an INH-NAD adduct (Zhang et al 1992). These adduct binds and inhibit physiological function of inhA enzyme. Inhibition of inhA blocks mycolic acid biosynthesis, thereby impairing the integrity of cell wall and eventually leading to cell death (Vilcheze et al 2000). Nearly 70-80% of drug resistance to INH results primarily from mutations in KatG. Consequently, novel InhA inhibitors like compounds of formula (I) that do not require activation by KatG are attractive drug candidates for treating TB.

TABLE 4

| | InhA genotype | Compound MIC$_{50}$ (μM) | | | |
| --- | --- | --- | --- | --- | --- |
| | | Pyridones | | | |
| Strain name | | PD12 | PD10 | Isoniazid | Ethionamide |
| M. smeg WT | WT inhA | 0.67 | 0.40 | >20 | >20 |
| SMEG-529-108-5X-Y5 | atg to att M161I | 2.92 | 4.21 | >20 | >20 |
| BCG WT | WT inhA | 0.37 | 0.02 | 0.30 | 17.00 |
| BCG-529-108-10X-2 | atg to gtc M161V | 27.88 | 3.02 | 1.27 | >60 |
| BCG-916-108-25X-B1 | atg to atc M161I | 21.52 | 3.2 | 1.48 | >60 |

What is claimed is:
1. A compound of Formula (I)

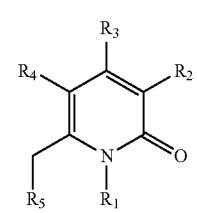

(I)

wherein
R$_1$ is H, methyl or ethyl;
R$_2$ is phenyl, wherein said phenyl is optionally substituted with one or more substituents independently selected from fluoro or chloro; provided that when said substituent is chloro, said chloro is on the meta or ortho position of said phenyl and the number of chloro substituent is not more than one;
R$_3$ is a structural formula selected from the group consisting of

(Ia)

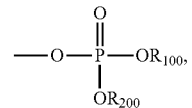

(Ib)

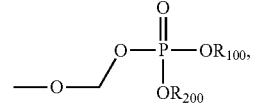

(Ic)

-continued

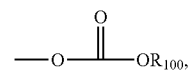
(Id)

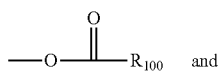
(Ie)

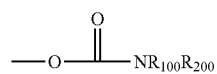
(If)

where $R_{100}$ and $R_{200}$ are each independently selected from the group consisting of H, $(C_1-C_6)$alkyl, and cycloalkyl;

$R_4$ is H or —C(=O)NH$_2$;

$R_5$ is selected from the group consisting of $(C_1-C_6)$ alkyl, cycloalkyl, and phenyl, optionally substituted with one or more independent $R_{300}$ substituents; and $R_{300}$ is selected from the group consisting of H, $(C_1-C_6)$alkyl, cycloalkyl, hydroxy, amino and F;

or a pharmaceutically acceptable salt thereof.

2. The compound of claim 1, or a pharmaceutically acceptable salt thereof, wherein $R_1$ is H.

3. The compound of claim 1, or a pharmaceutically acceptable salt thereof, wherein $R_2$ is phenyl.

4. The compound of claim 1, or a pharmaceutically acceptable salt thereof, wherein $R_3$ is (Ia).

5. The compound of claim 1, or a pharmaceutically acceptable salt thereof, wherein $R_3$ is (IC), and $R_{100}$ and $R_{200}$ are both H.

6. The compound of claim 1, or a pharmaceutically acceptable salt thereof, wherein $R_4$ is H.

7. The compound of claim 1, or a pharmaceutically acceptable salt thereof, wherein $R_5$ is $(C_1-C_6)$alkyl or phenyl.

8. The compound of claim 1, or a pharmaceutically acceptable salt thereof, wherein $R_5$ is cycloalkyl.

9. The compound of claim 1, or a pharmaceutically acceptable salt thereof, wherein $R_5$ is cyclohexane.

10. The compound of claim 1, or a pharmaceutically acceptable salt thereof, wherein $R_5$ is cyclohexane which is substituted with one or more substituents independently selected from $(C_1-C_6)$alkyl, cycloalkyl or F.

11. The compound of claim 1, or a pharmaceutically acceptable salt thereof, wherein $R_5$ is cyclohexane which is substituted with one or more substituents independently selected from methyl, cyclopropane or F.

12. The compound of claim 1, or a pharmaceutically acceptable salt thereof, wherein $R_5$ is cyclohexane which is substituted with two methyl substitutents.

13. The compound of claim 1, or a pharmaceutically acceptable salt thereof, selected from the group consisting of:

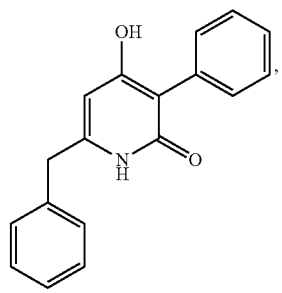

PD1

6-benzyl-4-hydroxy-3-phenylpyridin-2(1H)-one

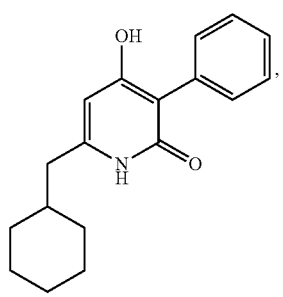

PD2

6-(cyclohexylmethyl)-4-hydroxy-3-phenylpyridin-2(1H)-one

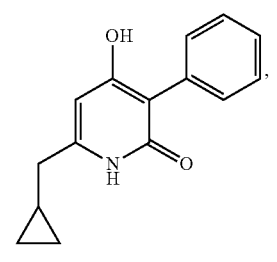

PD3

6-(cyclopropylmethyl)-4-hydroxy-3-phenylpyridin-2(1H)-one

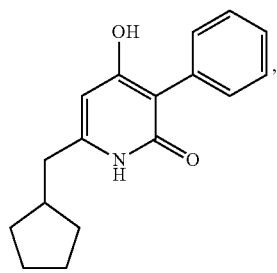

PD4

6-(cyclopentylmethyl)-4-hydroxy-3-phenylpyridin-2(1H)-one

-continued

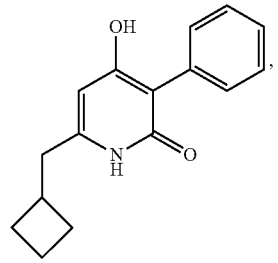

PD5

6-(cyclobutylmethyl)-4-hydroxy-3-
phenylpyridin-2(1H)-one

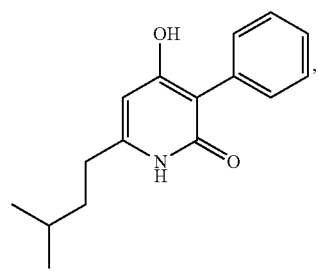

PD7

4-hydroxy-6-isopentyl-3-phenylpyridin-
2(1H)-one

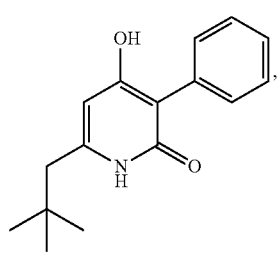

PD8

4-hydroxy-6-neopentyl-3-
phenylpyridin-2(1H)-one

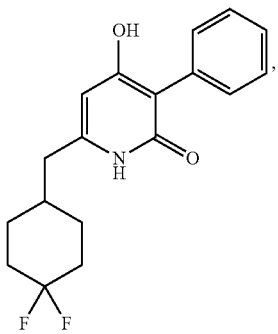

PD9

6-((4,4-difluorocyclohexyl)
methyl)-4-hydroxy-3-phenylpyridin-
2(1H)-one

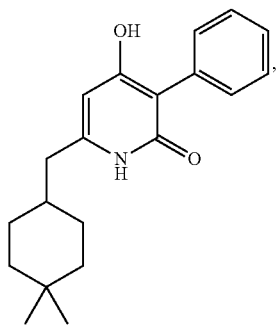

PD10

6-((4,4-dimethylcyclohexyl)
methyl)-4-hydroxy-3-
phenylpyridin-2(1H)-one

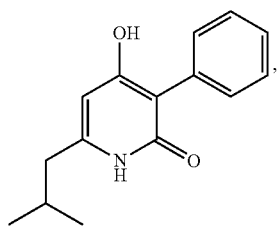

PD12

4-hydroxy-6-isobutyl-3-
phenylpyridin-2(1H)-one

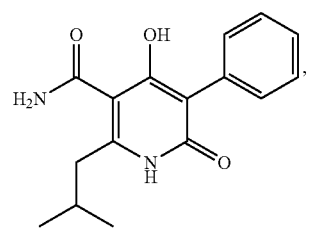

PD13

4-hydroxy-2-isobutyl-6-oxo-5-
phenyl-1,6-dihydropyridine-3-
carboxamide

PD14

3-(3-chlorophenyl)-4-hydroxy-6-
isobutylpyridin-2(1H)-one

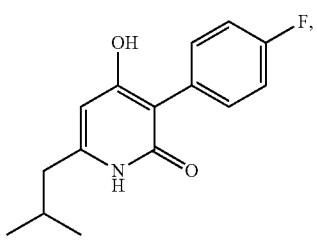

PD15

3-(4-fluorophenyl)-4-hydroxy-6-
isobutylpyridin-2(1H)-one 67  68
-continued  -continued

PD16

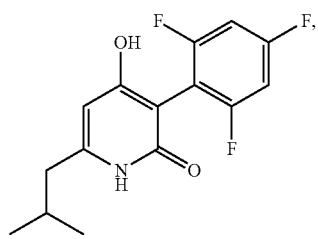

4-hydroxy-6-isobutyl-3-(2,4,6-
trifluorophenyl)pyridin-2(1H)-one

PD21

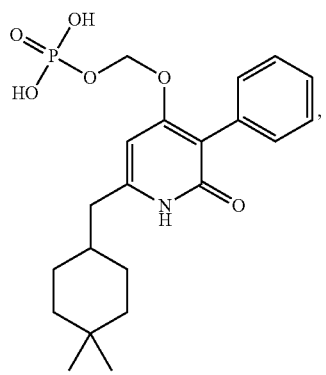

((6-((4,4-dimethylcyclohexyl)methyl)-2-
oxo-3-phenyl-1,2-dihydropyridin-4-
yl)oxy)methyl dihydrogen phosphate

PD17

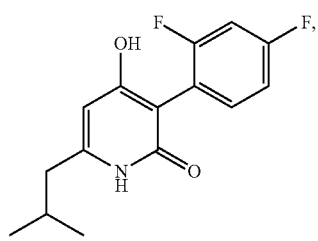

3-(2,4-difluorophenyl)-4-hydroxy-6-
isobutylpyridin-2(1H)-one

PD18

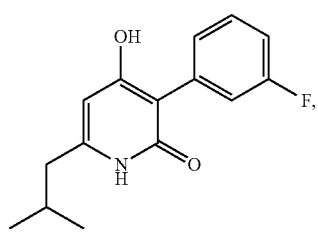

3-(3-fluorophenyl)-4-hydroxy-6-
isobutylpyridin-2(1H)-one

PD22

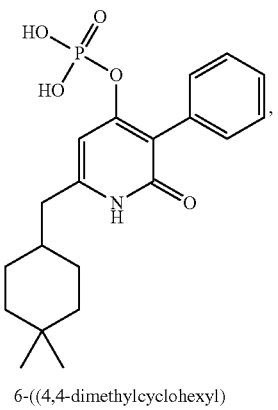

6-((4,4-dimethylcyclohexyl)
methyl)-2-oxo-3-phenyl-
1,2-dihydropyridin-
4-yl dihydrogen phosphate

PD19

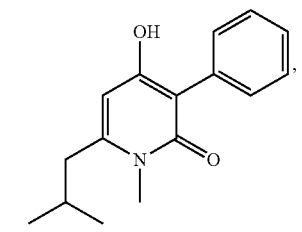

4-hydroxy-6-isobutyl-1-methyl-3-
phenylpyridin-2(1H)-one

PD20

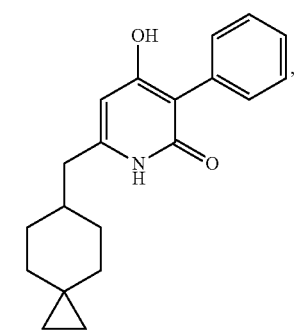

4-hydroxy-3-phenyl-6-
(spiro[2.5]octan-6-ylmethyl)pyridin-
2(1H)-one

PD23

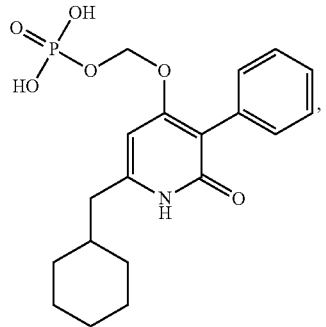

((6-cyclohexylmethyl)-2-oxo-3-
phenyl-1,2-dihydropyridin-4-
yl)oxy)methyl dihydrogen phosphate -continued

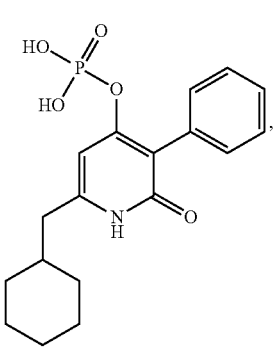

6-(cyclohexylmethyl)-2-oxo-3-phenyl-1,2-dihydropyridin-4-yl dihydrogen phosphate

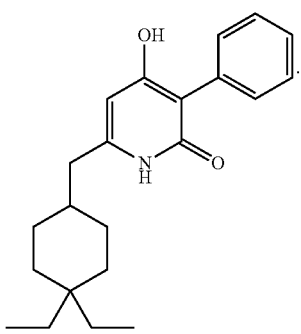

6-((4,4-diethylcyclohexyl)methyl)-4-hydroxy-3-phenylpyridin-2(1H)-one

14. The compound of claim 1, or a pharmaceutically acceptable salt thereof, wherein said compound has the following structure

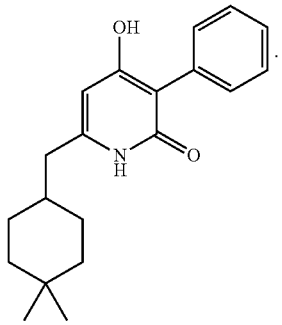 [SMILES: CC1(C)CCC(Cc2cc(O)c(-c3ccccc3)c(=O)[nH]2)CC1]

15. The compound of claim 1, or a pharmaceutically acceptable salt thereof, wherein said compound has the following structure

PD24

PD25

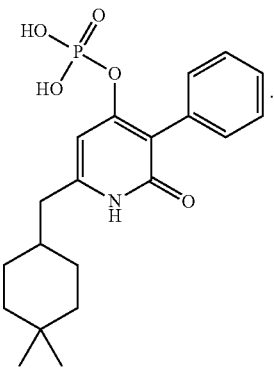 [SMILES: CC1(C)CCC(Cc2cc(OP(=O)(O)O)c(-c3ccccc3)c(=O)[nH]2)CC1]

16. The compound of claim 1, or a pharmaceutically acceptable salt thereof, wherein said compound has the following structure

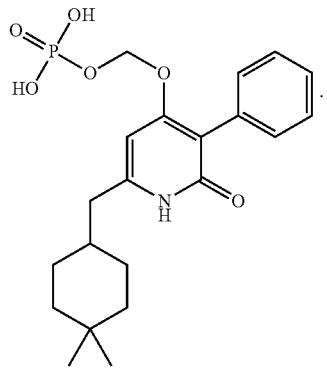 [SMILES: CC1(C)CCC(Cc2cc(OCOP(=O)(O)O)c(-c3ccccc3)c(=O)[nH]2)CC1]

17. A pharmaceutical composition comprising a compound of claim 1, or a pharmaceutically acceptable salt thereof, and a pharmaceutically acceptable carrier or excipient.

* * * * *